United States Patent
Xu et al.

(10) Patent No.: US 6,737,240 B1
(45) Date of Patent: *May 18, 2004

(54) METHODS OF SCREENING FOR A MULTI-DRUG RESISTANCE CONFERRING PEPTIDE

(75) Inventors: Ziang Xu, South San Francisco, CA (US); Donald Payan, Hillsborough, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/578,030

(22) Filed: May 24, 2000

Related U.S. Application Data

(60) Provisional application No. 60/136,018, filed on May 25, 1999.

(51) Int. Cl.[7] .............................................. G01N 33/53
(52) U.S. Cl. ................................ 435/7.1; 435/6; 435/4; 435/DIG. 3; 435/DIG. 2; 536/23.4; 536/23.1; 530/300
(58) Field of Search .................... 435/7.1, 6, 4, DIG. 3, 435/DIG. 2; 536/23.4, 23.1; 530/300

(56) References Cited

U.S. PATENT DOCUMENTS

| | | | | |
|---|---|---|---|---|
| 5,908,835 A | * | 6/1999 | Bissery | 514/33 |
| 6,210,917 B1 | * | 4/2001 | Carson et al. | 435/18 |

FOREIGN PATENT DOCUMENTS

| | | |
|---|---|---|
| JP | 05 317059 | 12/1993 |
| WO | 96/11207 A1 | 4/1996 |
| WO | 97/27212 A1 | 7/1997 |

OTHER PUBLICATIONS

Hofmann et al Rapid retroviral delivery if tetracycline–inducible genes in a single autoregulatory cassette. Proc.Natl. Acad. Sci. 92: 5185–5190.*

Fabbrizio, E. et al "Inhibition of mammalian cell proliferation by genetically selected peptide aptamers that functionally antagonize E2F activity", *Oncogene*, 18:4357–4363 (1999).

Wong, D.W., and Robertson, G.H., "High–affinity peptide ligands for pancreatic alpha–amylase by phage display", *Ann. N. Y. Acad. Sci.*, 864:555–557 (1998).

Bremnes, T. et al., Selection of phage displayed peptides from a random 10–mer library recognizing a peptide target, *Immunotechnology*, 4:21–28 (1998).

Kaye, S. B., "Multidrug resistance: clinical relevance in solid tumours and strategies for circumvention", *Curr. Opin. Oncol.*, 10 Suppl. 1, S15–19 (1998).

Hart, et al., "Flow cytometric assessment of multidrug resistance (MDR) phenotype in acute myeloid leukaemia", *Leuk. Lymphoma*, 11:239–248 (1993).

Yamaguchi, et al., Frequent expressions of P–glycoprotein/MDR1 by nasal T–cell lymphoma cells, *Cancer*, 76:2351–2356 (1995).

Bello–Reuss, E. and Ernest, S., Expression and function of P–glycoprotein in human mesangial cells:; *Am. J. Physiol.*, C1351–1358 (1994).

Chin, et al., "Regulation of mdr RNA levels in response to cytotoxic drugs in rodent cells", *Cell Growth Differ.*, 8:361–365 (1990).

Parekh, et al., "Aquisition of taxol resistance via P–glycoprotein–and non–P–glycoprotein–mediated mechanisms in human ovarian carcinoma cells", *Biochem. Pharmacol.*, 53:461–470 (1997).

Fardel, et al., "Constitutive expression of functional P–glycoprotein in rat hepatoma cells", *Eur. J. Biochem.*, 219:521–528 (1994).

Leith, C., "Multidrug resistance in leukemia", *Curr. Opin. Hematol.*, 5:287–291 (1998).

* cited by examiner

*Primary Examiner*—T. D. Wessendorf
(74) *Attorney, Agent, or Firm*—James S. Keddie; Carol L. Francis; James J. Diehl

(57) ABSTRACT

The invention relates generally to methods of screening for drugs which bind to and/or regulate cellular proteins involved in drug resistance, particularly resistance of tumor cells to chemotherapeutic agents.

9 Claims, 11 Drawing Sheets

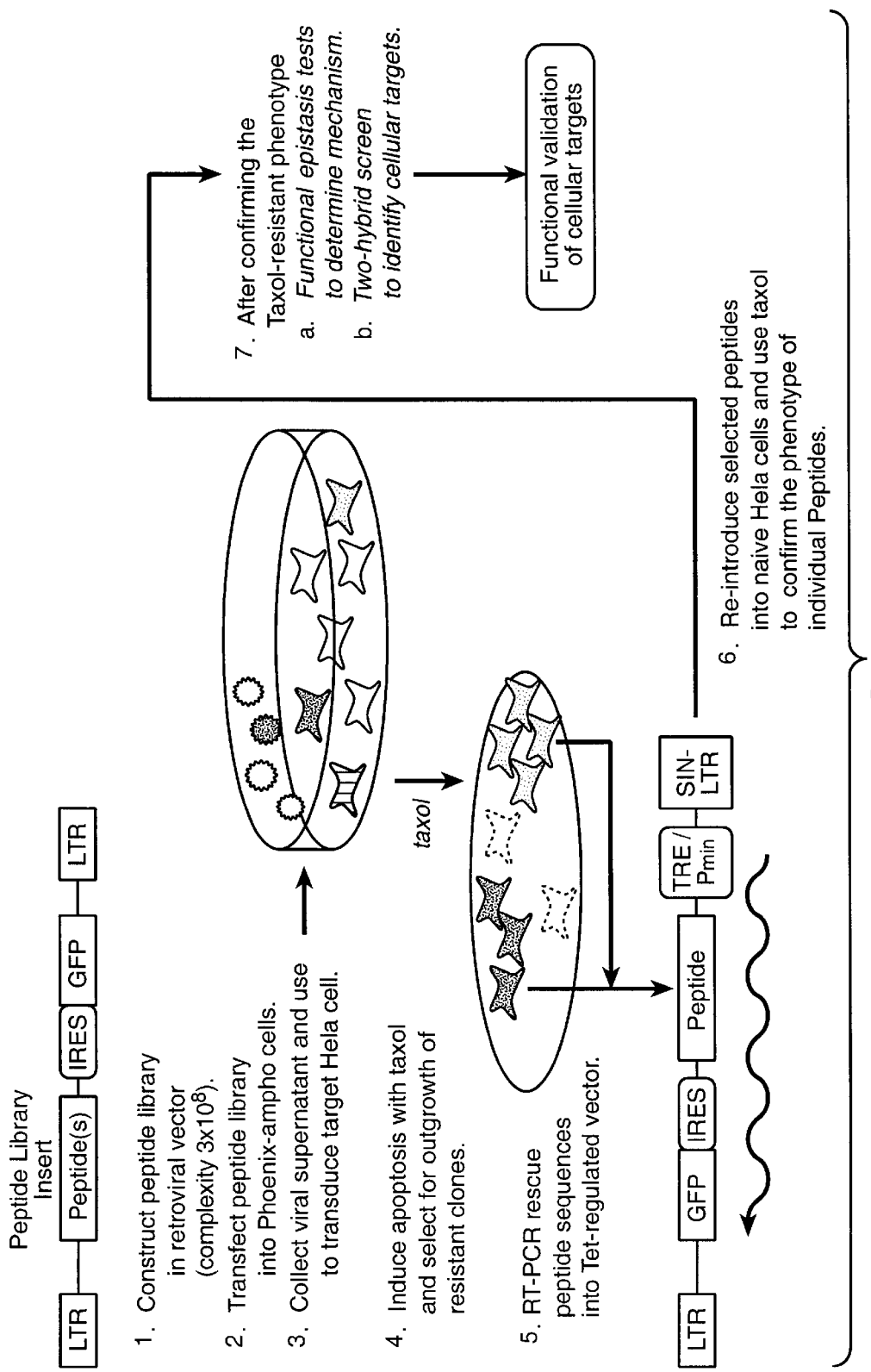
FIG._1A

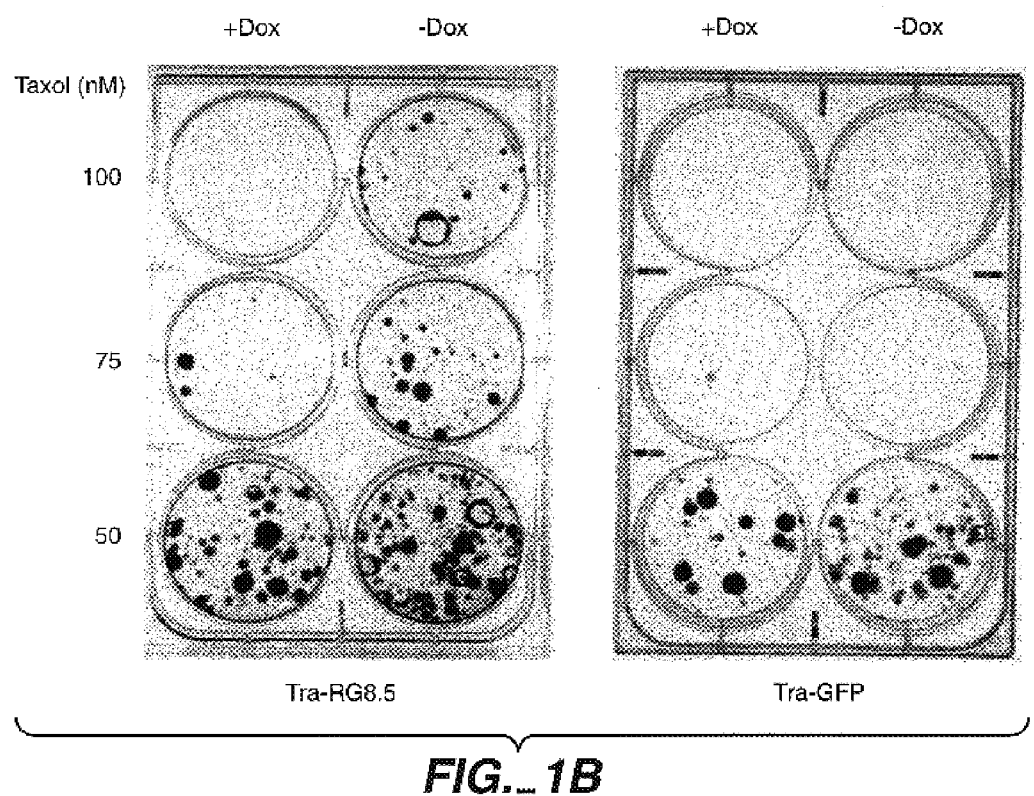
FIG._1B

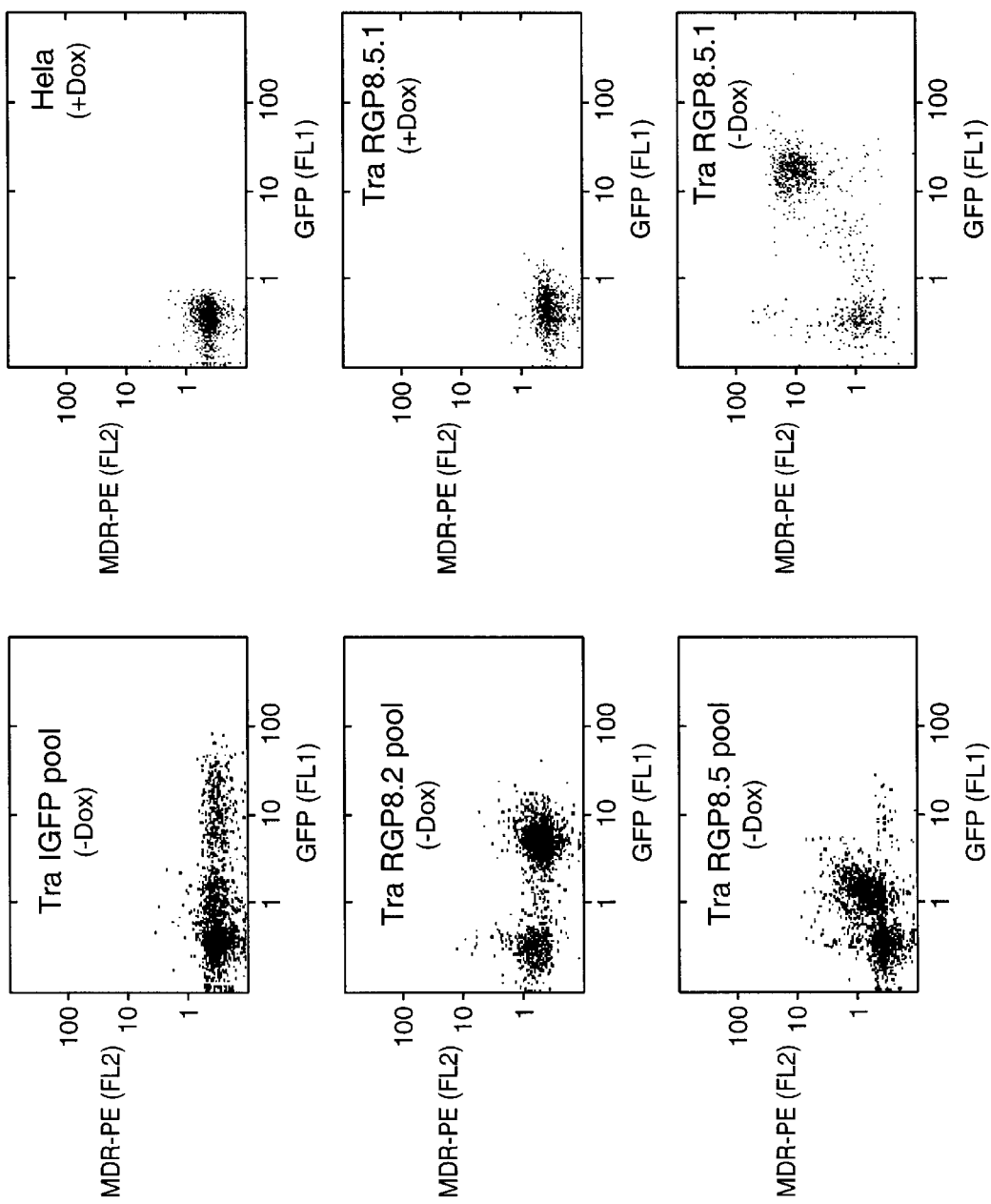
FIG._2A

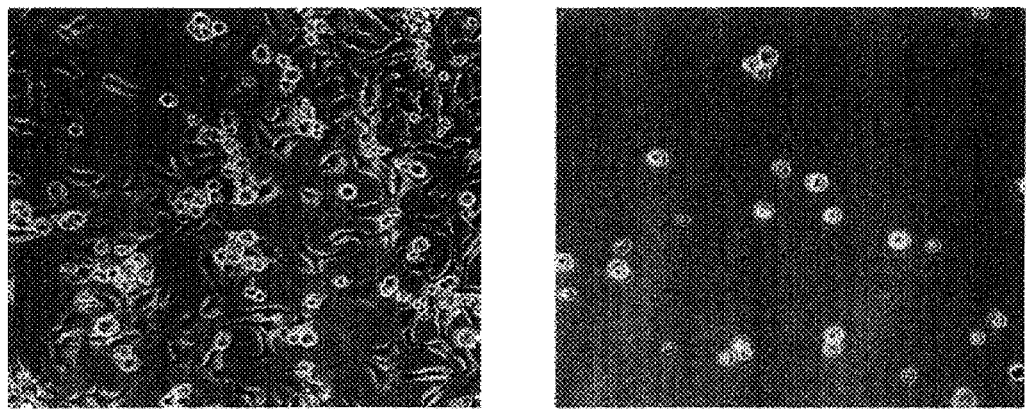
FIG._2B

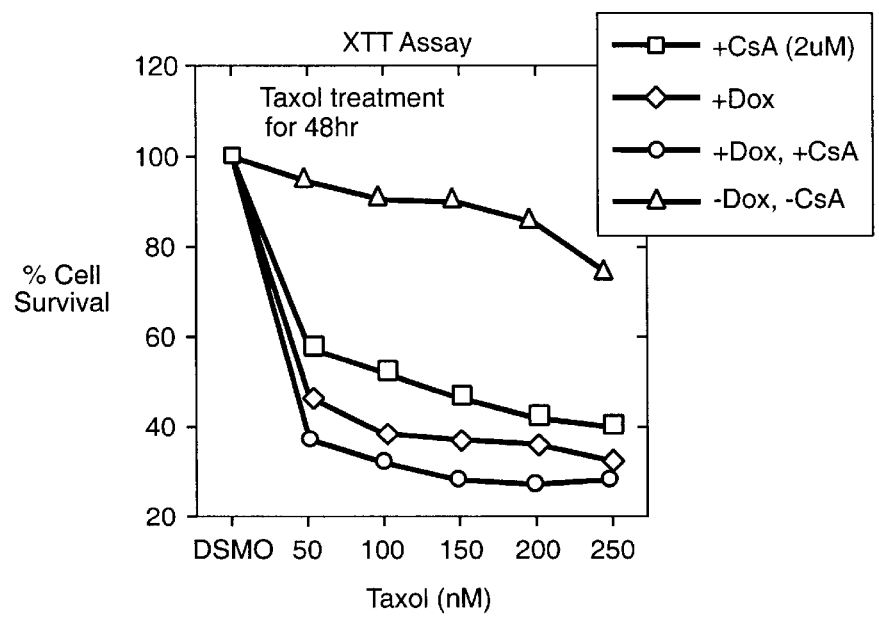
FIG._2C
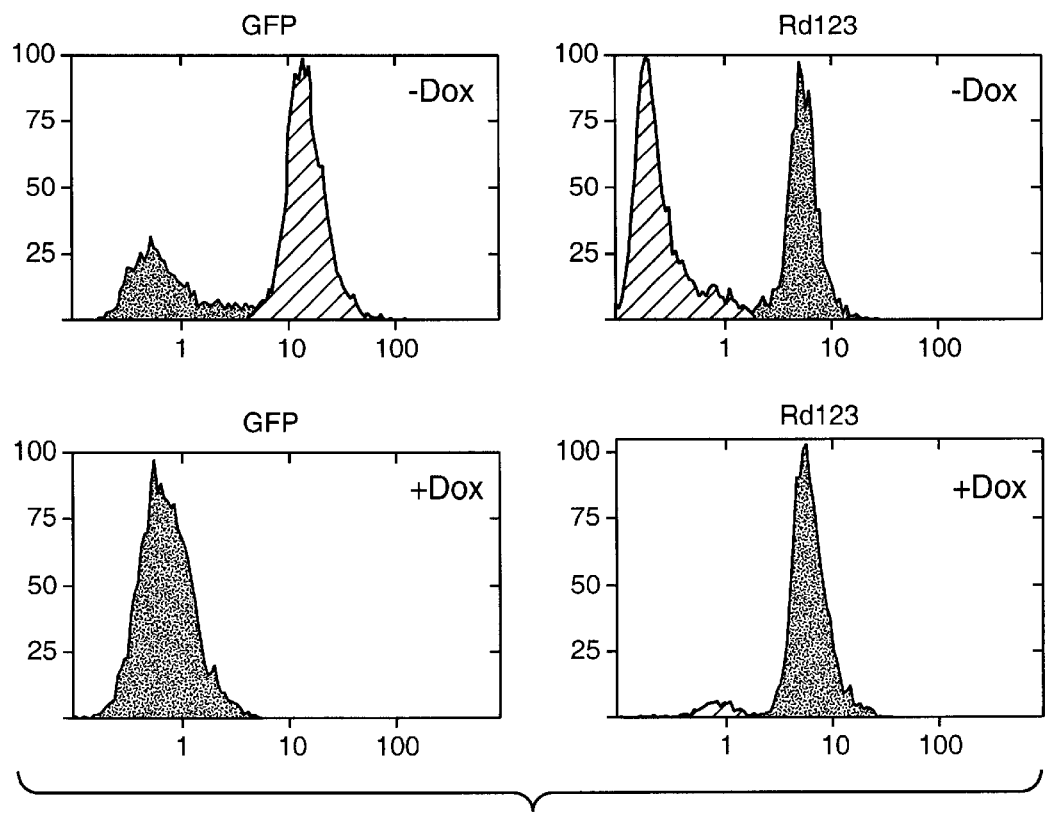
FIG._2D

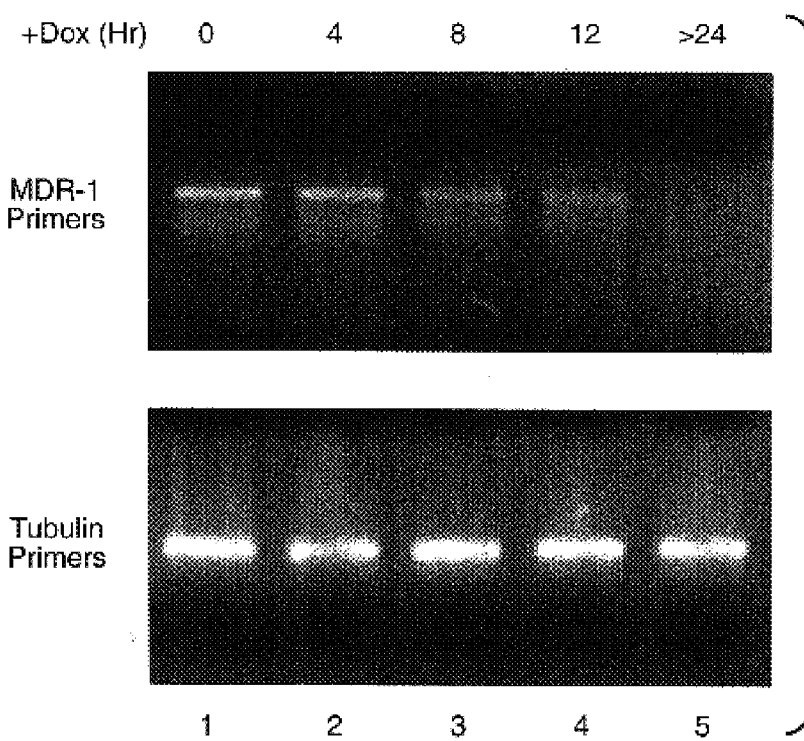
FIG._3
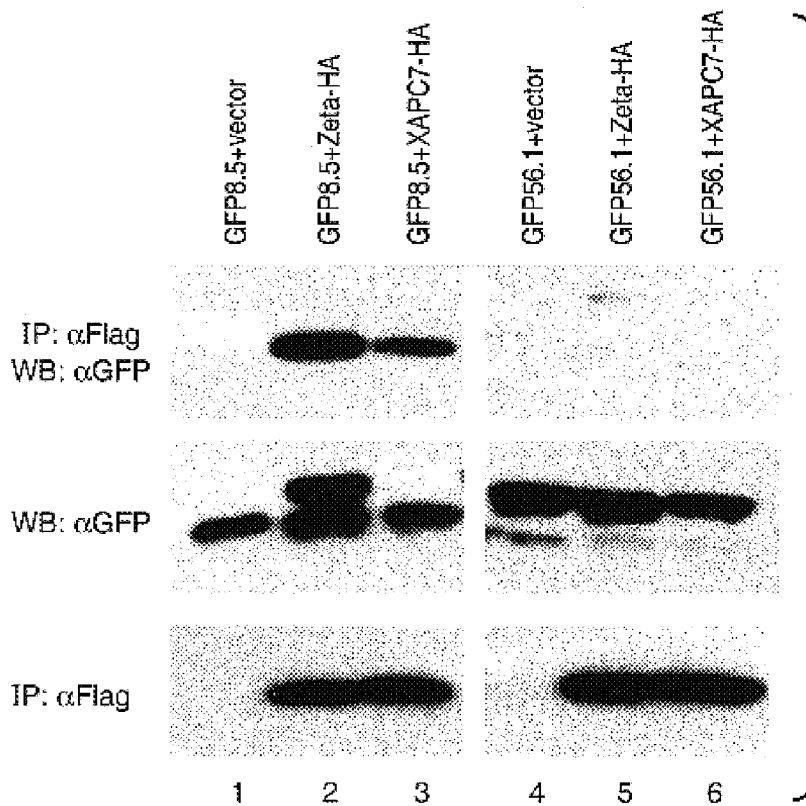
FIG._4A

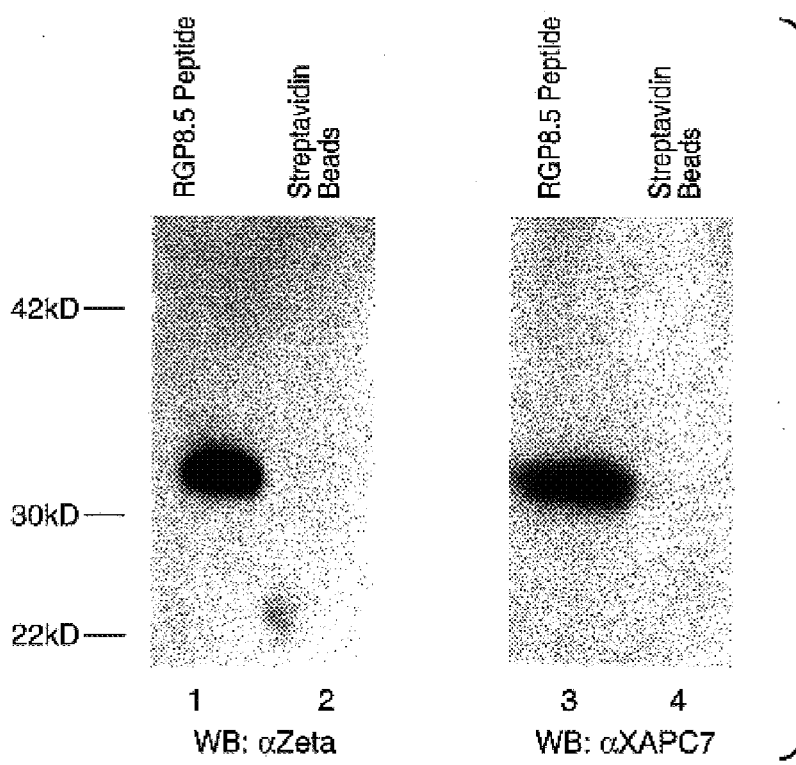
FIG._4B
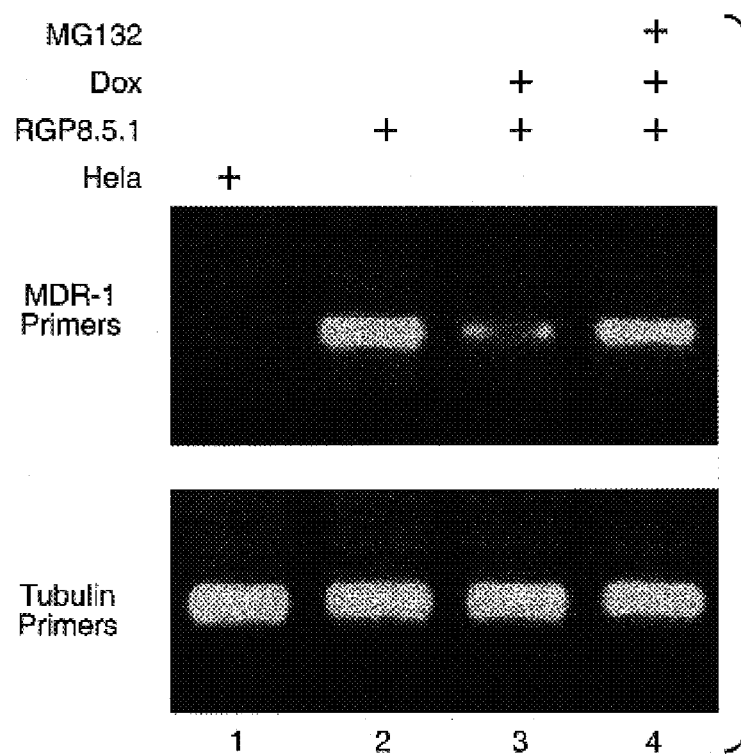
FIG._5A

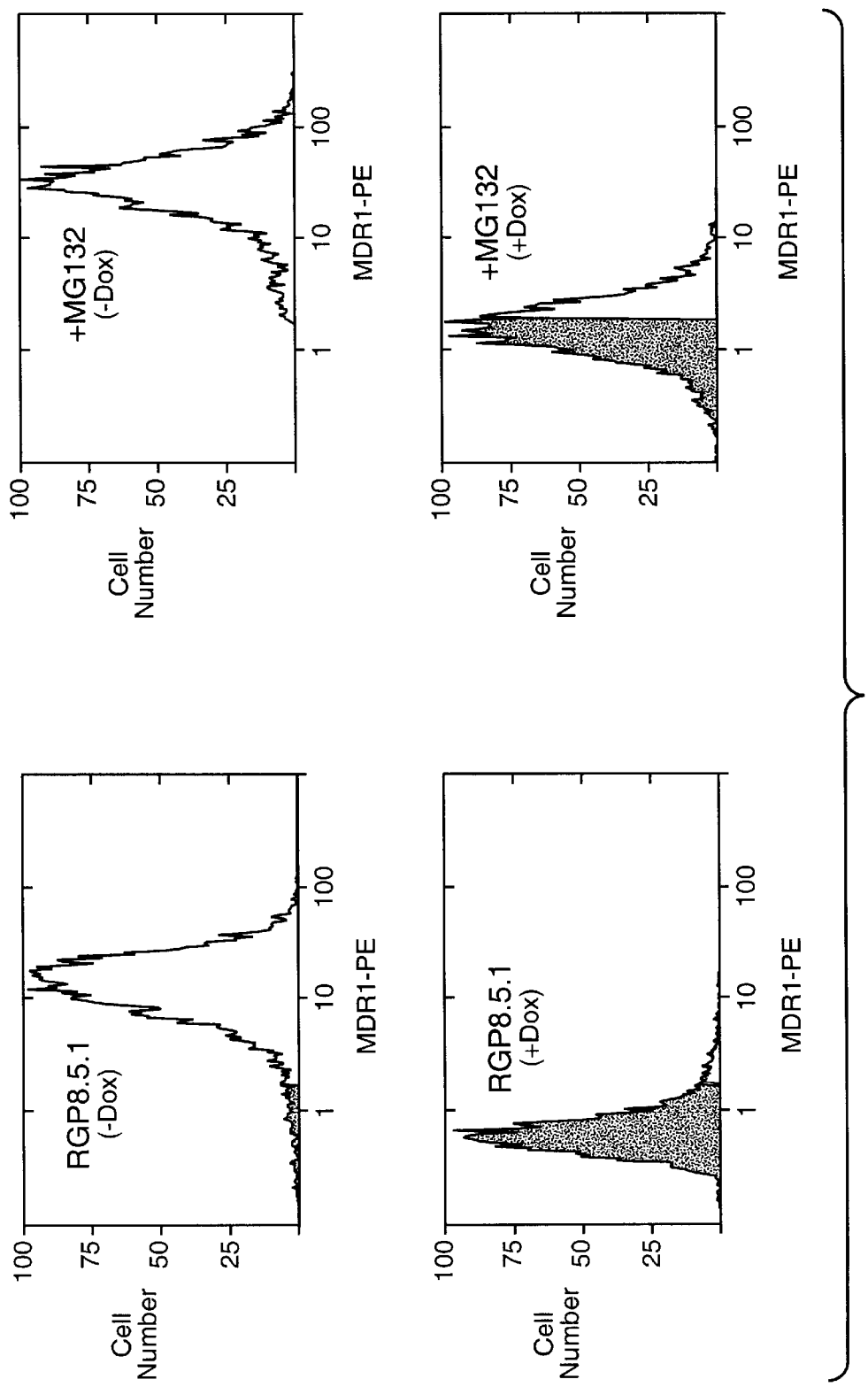
FIG._5B

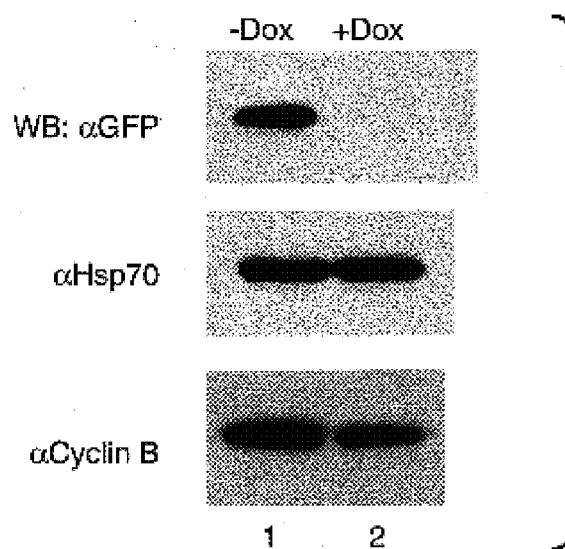
FIG._6A
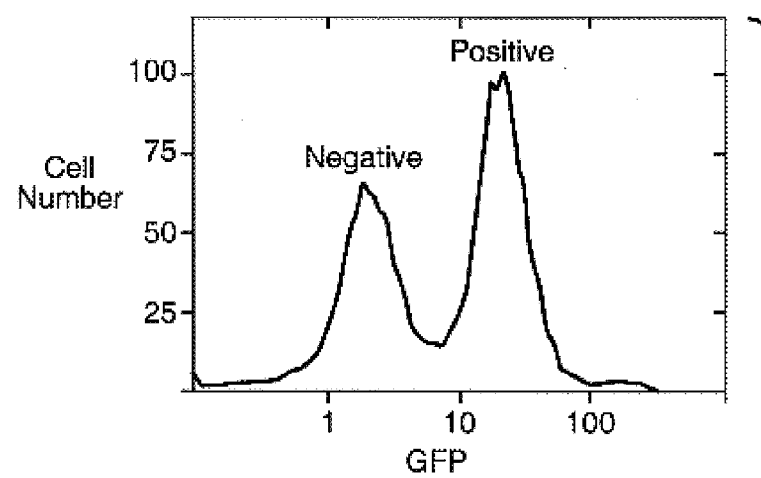
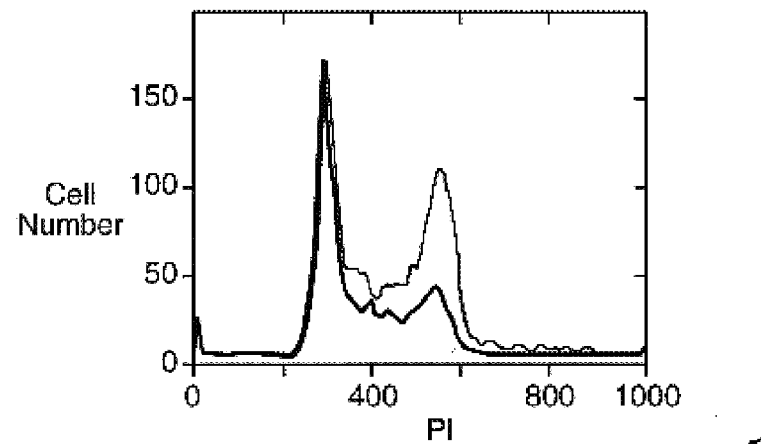
FIG._6B

SEQUENCE ID NO:1:

MGEFLIVKVWGRMVCWVLVVRRFVLVIVLENSLSSNQGPPZ

FIG._7A

SEQUENCE ID NO:2:

ATGGGCGAGTTTTTGATTGTTAAGGTCTGGGGTC
GCATGGTTTGTTGGGTTCTCGTTGTGCGTCGTTTTGTCCTCGTCATTGTGTTGGAGAATTCC
TTATCGTCAAATCAGGGCCCTCCTTAA

FIG._7B

SEQUENCE ID NO:3:

```
ggcacgaggc ggccgcccgc cggcatgagc tacgaccgcg ccatcaccgt
cttctcgccc gacggccacc tcttccaagt ggagtacgcg caggaggccg
tcaagaaggg ctcgaccgcg gttggtgttc gaggaagaga cattgttgtt
cttggtgtgg agaagaagtc agtggccaaa ctgcaggatg aaagaacagt
gcggaagatc tgtgctttgg atgacaacgt ctgcatggcc tttgcaggcc
tcaccgccga tgcaaggata gtcatcaaca gggcccgggt ggagtgccag
agccaccggc tgactgtaga ggacccggtc actgtggagt acatcacccg
ctacatcgcc agtctgaagc agcgttatac gcagagcaat gggcgcaggc
cgtttggcat ctctgccctc atcgtgggtt tcgactttga tgcactcct
aggctctatc agactgaccc ctcgggcaca taccatgcct ggaaggccaa
tgccataggc cggggtgcca agtcagtgcg cgagttcctg gagaagaact
atactgacga agccattgaa acagatgatc tgaccattaa gctggtgatc
aaggcactcc tggaagtggt tcagtcaggt ggcaaaaaca ttgaacttgc
tgtcatgagg cgagatcaat ccctcaagat tttaaatcct gaagaaattg
agaagtatgt tgctgaaatt gaaaagaaa aagaagaaaa cgaaaagaag
aaacaaaaga aagcatcatg atgaataaaa tgtctttgct tgtaattttt
aaattcatat caatcatgga tgagtctcga tgtgtaggcc tttccattcc
atttattcac actgagtgtc ctacaataaa cttccgtatt ttt
```

FIG._8A

SEQUENCE ID NO:4:

>gi|2555136|gb|AAB81515.1| proteasome subunit XAPC7

MSYDRAITVFSPDGHLFQVEYAQEAVKKGSTAVGVRGRDIVVLGVEKKSVAKLQDERTVRKICALDDNVC
MAFAGLTADARIVINRARVECQSHRLTVEDPVTVEYITRYIASLKQRYTQSNGRRPFGISALIVGFDFDG
TPRLYQTDPSGTYHAWKANAIGRGAKSVREFLEKNYTDEAIETDDLTIKLVIKALLEVVQSGGKNIELAV
MRRDQSLKILNPEEIEKYVAEIEKEKEENEKKKQKKAS

FIG._8B

SEQUENCE ID NO:5:

```
ctgcctcctc ctaccctcgc catgtttctt acccggtctg agtacgacag
gggcgtgaat acttttctc ccgaaggaag attatttcaa gtggaatatg
acattgaggc tatcaagctt ggttctacag ccattgggat ccagacatca
gagggtgtgt gcctagctgt ggagaagaga attacttccc cactgatgga
gcccagcagc attgagaaaa ttgtagagat tgatgctcac ataggttgtg
ccatgagtgg gctaattgct gatgctaaga ctttaattga taaagccaga
gtggagacac agaaccactg gttcacctac aatgagacaa tgacagtgga
gagtgtgacc caagctgtgt ccaatctggc tttgcagttt ggagaagaag
atgcagatcc aggtgccatg tctcgtccct tggagtagc attattattt
ggaggagttg atgagaaagg accccagctg tttcatatgg acccatctgg
gacctttgta cagtgtgatg ctcgagcaat tggctctgct tcagagggtg
cccagagctc cttgcaagaa ctttaccaca agtctatgac tttgaaagaa
gccatcaagt cttcactcat catcctcaaa caagtaatgg aggagaagct
gaatgcaaca acattgagc tagccacagt gcagcctggc cagaatttcc
acatgttcac aaaggaagaa cttgaagagg ttatcaagga catttaagga
atcctgatcc tcagaacttc tctgggacaa tttcagttct aataatgtcc
ttaaatttta tttccagctc ctgttccttg gaaatctcc attgtatgtg
catttttaa atgatgtctg tacataaagg cagttctgaa ataaagaaaa
ttttaaaata aaaaaaaaa aaaaaaaaa aaaaaaaaa aaaaaaaaa
aaaaaaaa
```

FIG._8C

SEQUENCE ID NO:6:

MFLTRSEYDRGVNTFSPEGRLFQVEYDIEAIKLGSTAIGIQTSEGVCLAVEKRITSPLMEPSSIEKIVEI
DAHIGCAMSGLIADAKTLIDKARVETQNHWFTYNETMTVESVTQAVSNLALQFGEEDADPGAMSRPFGVA
LLFGGVDEKGPQLFHMDPSGTFVQCDARAIGSASEGAQSSLQELYHKSMTLKEAIKSSLIILKQVMEEKL
NATNIELATVQPGQNFHMFTKEELEEVIKDI

FIG._8D

SEQUENCE LISTING

```
<160> NUMBER OF SEQ ID NOS:  51

<210> SEQ ID NO 1
<211> LENGTH: 41
<212> TYPE: PRT
<213> ORGANISM: Artificial Sequence
<220> FEATURE:
<221> NAME/KEY: UNSURE
<222> LOCATION: (41)
<223> OTHER INFORMATION: Glx at position 41 can be Glutamic acid or
      Glutamine.
<223> OTHER INFORMATION: Description of Artificial Sequence:  Synthetic

<400> SEQUENCE: 1

Met Gly Glu Phe Leu Ile Val Lys Val Trp Gly Arg Met Val Cys Trp
  1               5                  10                  15

Val Leu Val Val Arg Arg Phe Val Leu Val Ile Val Leu Glu Asn Ser
             20                  25                  30

Leu Ser Ser Asn Gln Gly Pro Pro Glx
         35                  40

<210> SEQ ID NO 2
<211> LENGTH: 123
<212> TYPE: DNA
<213> ORGANISM: Artificial Sequence
<220> FEATURE:
<223> OTHER INFORMATION: Description of Artificial Sequence:  Synthetic

<400> SEQUENCE: 2
atgggcgagt ttttgattgt taaggtctgg ggtcgcatgg tttgttgggt tctcgttgtg      60
cgtcgttttg tcctcgtcat tgtgttggag aattccttat cgtcaaatca gggccctcct     120
```

-continued

```
taa                                                              123

<210> SEQ ID NO 3
<211> LENGTH: 893
<212> TYPE: DNA
<213> ORGANISM: Homo sapiens

<400> SEQUENCE: 3
ggcacgaggc ggccgcccgc cggcatgagc tacgaccgcg ccatcaccgt cttctcgccc    60
gacggccacc tcttccaagt ggagtacgcg caggaggccg tcaagaaggg ctcgaccgcg   120
gttggtgttc gaggaagaga cattgttgtt cttggtgtgg agaagaagtc agtggccaaa   180
ctgcaggatg aaagaacagt gcggaagatc tgtgctttgg atgacaacgt ctgcatggcc   240
tttgcaggcc tcaccgccga tgcaaggata gtcatcaaca gggcccgggt ggagtgccag   300
agccaccggc tgactgtaga ggacccggtc actgtggagt acatcacccg ctacatcgcc   360
agtctgaagc agcgttatac gcagagcaat gggcgcaggc cgtttggcat tctgccctc    420 atcgtgggtt tcgactttga tggcactcct aggctctatc agactgaccc ctcgggcaca   480
taccatgcct ggaaggccaa tgccataggc cggggtgcca agtcagtgcg cgagttcctg   540
gagaagaact atactgacga agccattgaa acagatgatc tgaccattaa gctggtgatc   600
aaggcactcc tggaagtggt tcagtcaggt ggcaaaaaca ttgaacttgc tgtcatgagg   660
cgagatcaat ccctcaagat tttaaatcct gaagaaattg agaagtatgt tgctgaaatt   720 gaaaagaaa aagaagaaaa cgaaaagaag aaacaaaaga aagcatcatg atgaataaaa   780
tgtctttgct tgtaattttt aaattcatat caatcatgga tgagtctcga tgtgtaggcc   840
tttccattcc atttattcac actgagtgtc ctacaataaa cttccgtatt ttt          893

<210> SEQ ID NO 4
<211> LENGTH: 248
<212> TYPE: PRT
<213> ORGANISM: Homo sapiens

<400> SEQUENCE: 4

Met Ser Tyr Asp Arg Ala Ile Thr Val Phe Ser Pro Asp Gly His Leu
  1               5                  10                  15

Phe Gln Val Glu Tyr Ala Gln Glu Ala Val Lys Lys Gly Ser Thr Ala
                 20                  25                  30

Val Gly Val Arg Gly Arg Asp Ile Val Val Leu Gly Val Glu Lys Lys
             35                  40                  45

Ser Val Ala Lys Leu Gln Asp Glu Arg Thr Val Arg Lys Ile Cys Ala
         50                  55                  60

Leu Asp Asp Asn Val Cys Met Ala Phe Ala Gly Leu Thr Ala Asp Ala
 65                  70                  75                  80

Arg Ile Val Ile Asn Arg Ala Arg Val Glu Cys Gln Ser His Arg Leu
                 85                  90                  95

Thr Val Glu Asp Pro Val Thr Val Glu Tyr Ile Thr Arg Tyr Ile Ala
                100                 105                 110

Ser Leu Lys Gln Arg Tyr Thr Gln Ser Asn Gly Arg Arg Pro Phe Gly
            115                 120                 125

Ile Ser Ala Leu Ile Val Gly Phe Asp Phe Asp Gly Thr Pro Arg Leu
        130                 135                 140

Tyr Gln Thr Asp Pro Ser Gly Thr Tyr His Ala Trp Lys Ala Asn Ala
145                 150                 155                 160
```

```
Ile Gly Arg Gly Ala Lys Ser Val Arg Glu Phe Leu Glu Lys Asn Tyr
                165                 170                 175

Thr Asp Glu Ala Ile Glu Thr Asp Asp Leu Thr Ile Lys Leu Val Ile
            180                 185                 190

Lys Ala Leu Leu Glu Val Val Gln Ser Gly Gly Lys Asn Ile Glu Leu
        195                 200                 205

Ala Val Met Arg Arg Asp Gln Ser Leu Lys Ile Leu Asn Pro Glu Glu
    210                 215                 220

Ile Glu Lys Tyr Val Ala Glu Ile Glu Lys Glu Lys Glu Asn Glu
225                 230                 235                 240

Lys Lys Lys Gln Lys Lys Ala Ser
                245

<210> SEQ ID NO 5
<211> LENGTH: 959
<212> TYPE: DNA
<213> ORGANISM: Homo sapiens

<400> SEQUENCE: 5
ctgcctcctc ctaccctcgc catgtttctt acccggtctg agtacgacag gggcgtgaat      60 acttttctc ccgaaggaag attatttcaa gtggaatatg acattgaggc tatcaagctt     120
ggttctacag ccattgggat ccagacatca gagggtgtgt gcctagctgt ggagaagaga     180
attacttccc cactgatgga gcccagcagc attgagaaaa ttgtagagat tgatgctcac     240
ataggttgtg ccatgagtgg gctaattgct gatgctaaga ctttaattga taaagccaga     300
gtggagacac agaaccactg gttcacctac aatgagacaa tgacagtgga gagtgtgacc     360
caagctgtgt ccaatctggc tttgcagttt ggagaagaag atgcagatcc aggtgccatg     420
tctcgtccct ttggagtagc attattattt ggaggagttg atgagaaagg accccagctg     480
tttcatatgg acccatctgg gacctttgta cagtgtgatg ctcgagcaat ggctctgct     540 tcagagggtg cccagagctc cttgcaagaa ctttaccaca gtctatgac tttgaaagaa     600 gccatcaagt cttcactcat catccctcaaa caagtaatgg aggagaagct gaatgcaaca     660
aacattgagc tagccacagt gcagcctggc cagaatttcc acatgttcac aaaggaagaa     720
cttgaagagg ttatcaagga catttaagga atcctgatcc tcagaacttc tctgggacaa     780
tttcagttct aataatgtcc ttaaatttta tttccagctc ctgttccttg gaaaatctcc     840
attgtatgtg catttttaa atgatgtctg tacataaagg cagttctgaa ataaagaaaa     900
ttttaaaata aaaaaaaaa aaaaaaaaa aaaaaaaaa aaaaaaaaa aaaaaaaa            959

<210> SEQ ID NO 6
<211> LENGTH: 241
<212> TYPE: PRT
<213> ORGANISM: Homo sapiens

<400> SEQUENCE: 6

Met Phe Leu Thr Arg Ser Glu Tyr Asp Arg Gly Val Asn Thr Phe Ser
  1               5                  10                  15

Pro Glu Gly Arg Leu Phe Gln Val Glu Tyr Asp Ile Glu Ala Ile Lys
             20                  25                  30

Leu Gly Ser Thr Ala Ile Gly Ile Gln Thr Ser Glu Gly Val Cys Leu
         35                  40                  45

Ala Val Glu Lys Arg Ile Thr Ser Pro Leu Met Glu Pro Ser Ser Ile
     50                  55                  60

Glu Lys Ile Val Glu Ile Asp Ala His Ile Gly Cys Ala Met Ser Gly
```

```
                65                  70                  75                  80
Leu Ile Ala Asp Ala Lys Thr Leu Ile Asp Lys Ala Arg Val Glu Thr
                    85                  90                  95

Gln Asn His Trp Phe Thr Tyr Asn Glu Thr Met Thr Val Glu Ser Val
                100                 105                 110

Thr Gln Ala Val Ser Asn Leu Ala Leu Gln Phe Gly Glu Asp Ala
            115                 120                 125

Asp Pro Gly Ala Met Ser Arg Pro Phe Gly Val Ala Leu Leu Phe Gly
            130                 135                 140

Gly Val Asp Glu Lys Gly Pro Gln Leu Phe His Met Asp Pro Ser Gly
145                 150                 155                 160

Thr Phe Val Gln Cys Asp Ala Arg Ala Ile Gly Ser Ala Ser Glu Gly
                165                 170                 175

Ala Gln Ser Ser Leu Gln Glu Leu Tyr His Lys Ser Met Thr Leu Lys
            180                 185                 190

Glu Ala Ile Lys Ser Ser Leu Ile Ile Leu Lys Gln Val Met Glu Glu
            195                 200                 205

Lys Leu Asn Ala Thr Asn Ile Glu Leu Ala Thr Val Gln Pro Gly Gln
            210                 215                 220

Asn Phe His Met Phe Thr Lys Glu Glu Leu Glu Glu Val Ile Lys Asp
225                 230                 235                 240

Ile

<210> SEQ ID NO 7
<211> LENGTH: 61
<212> TYPE: PRT
<213> ORGANISM: Artificial Sequence
<220> FEATURE:
<223> OTHER INFORMATION: Description of Artificial Sequence: coiled-
      coil structure

<400> SEQUENCE: 7

Met Gly Cys Ala Ala Leu Glu Ser Glu Val Ser Ala Leu Glu Ser Glu
1               5                   10                  15

Val Ala Ser Leu Glu Ser Glu Val Ala Ala Leu Gly Arg Gly Asp Met
            20                  25                  30

Pro Leu Ala Ala Val Lys Ser Lys Leu Ser Ala Val Lys Ser Lys Leu
        35                  40                  45

Ala Ser Val Lys Ser Lys Leu Ala Ala Cys Gly Pro Pro
    50                  55                  60

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Loop
      structure

<400> SEQUENCE: 8

Gly Arg Gly Asp Met Pro
1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Randomized
      peptide
```

```
<221> NAME/KEY: UNSURE
<222> LOCATION: (1)..(5)
<223> OTHER INFORMATION: Xaa at positions 1 through 5 can be any amino
      acid residue.

<400> SEQUENCE: 9

Xaa Xaa Xaa Xaa Xaa
 1               5

<210> SEQ ID NO 10
<211> LENGTH: 69
<212> TYPE: PRT
<213> ORGANISM: Artificial Sequence
<220> FEATURE:
<223> OTHER INFORMATION: Description of Artificial Sequence:  Minibody
      presentation structure

<400> SEQUENCE: 10

Met Gly Arg Asn Ser Gln Ala Thr Ser Gly Phe Thr Phe Ser His Phe
 1               5                  10                  15

Tyr Met Glu Trp Val Arg Gly Gly Tyr Ile Ala Ala Ser Arg His
             20                  25                  30

Lys His Asn Lys Tyr Thr Thr Glu Tyr Ser Ala Ser Val Lys Gly Arg
             35                  40                  45

Tyr Ile Val Ser Arg Asp Thr Ser Gln Ser Ile Leu Tyr Leu Gln Lys
         50                  55                  60

Lys Lys Gly Pro Pro
 65

<210> SEQ ID NO 11
<211> LENGTH: 7
<212> TYPE: PRT
<213> ORGANISM: monkey virus

<400> SEQUENCE: 11

Pro Lys Lys Lys Arg Lys Val
 1               5

<210> SEQ ID NO 12
<211> LENGTH: 6
<212> TYPE: PRT
<213> ORGANISM: Homo sapiens

<400> SEQUENCE: 12

Ala Arg Arg Arg Arg Pro
 1               5

<210> SEQ ID NO 13
<211> LENGTH: 10
<212> TYPE: PRT
<213> ORGANISM: Mus musculus

<400> SEQUENCE: 13

Glu Glu Val Gln Arg Lys Arg Gln Lys Leu
 1               5                  10

<210> SEQ ID NO 14
<211> LENGTH: 9
<212> TYPE: PRT
<213> ORGANISM: Mus musculus

<400> SEQUENCE: 14

Glu Glu Lys Arg Lys Arg Thr Tyr Glu
 1               5
```

<210> SEQ ID NO 15
<211> LENGTH: 20
<212> TYPE: PRT
<213> ORGANISM: African clawed toad

<400> SEQUENCE: 15

Ala Val Lys Arg Pro Ala Ala Thr Lys Lys Ala Gly Gln Ala Lys Lys
 1               5                  10                  15

Lys Lys Leu Asp
            20

<210> SEQ ID NO 16
<211> LENGTH: 31
<212> TYPE: PRT
<213> ORGANISM: Mus musculus

<400> SEQUENCE: 16

Met Ala Ser Pro Leu Thr Arg Phe Leu Ser Leu Asn Leu Leu Leu Leu
 1               5                  10                  15

Gly Glu Ser Ile Leu Gly Ser Gly Glu Ala Lys Pro Gln Ala Pro
            20                  25                  30

<210> SEQ ID NO 17
<211> LENGTH: 21
<212> TYPE: PRT
<213> ORGANISM: Homo sapiens

<400> SEQUENCE: 17

Met Ser Ser Phe Gly Tyr Arg Thr Leu Thr Val Ala Leu Phe Thr Leu
 1               5                  10                  15

Ile Cys Cys Pro Gly
            20

<210> SEQ ID NO 18
<211> LENGTH: 51
<212> TYPE: PRT
<213> ORGANISM: Mus musculus

<400> SEQUENCE: 18

Pro Gln Arg Pro Glu Asp Cys Arg Pro Arg Gly Ser Val Lys Gly Thr
 1               5                  10                  15

Gly Leu Asp Phe Ala Cys Asp Ile Tyr Ile Trp Ala Pro Leu Ala Gly
            20                  25                  30

Ile Cys Val Ala Leu Leu Leu Ser Leu Ile Ile Thr Leu Ile Cys Tyr
                35                  40                  45

His Ser Arg
    50

<210> SEQ ID NO 19
<211> LENGTH: 33
<212> TYPE: PRT
<213> ORGANISM: Homo sapiens

<400> SEQUENCE: 19

Met Val Ile Ile Val Thr Val Val Ser Val Leu Leu Ser Leu Phe Val
 1               5                  10                  15

Thr Ser Val Leu Leu Cys Phe Ile Phe Gly Gln His Leu Arg Gln Gln
            20                  25                  30

Arg

```
<210> SEQ ID NO 20
<211> LENGTH: 37
<212> TYPE: PRT
<213> ORGANISM: Rat

<400> SEQUENCE: 20
```

Pro Asn Lys Gly Ser Gly Thr Thr Ser Gly Thr Thr Arg Leu Leu Ser
 1               5                  10                  15

Gly His Thr Cys Phe Thr Leu Thr Gly Leu Leu Gly Thr Leu Val Thr
            20                  25                  30

Met Gly Leu Leu Thr
        35

```
<210> SEQ ID NO 21
<211> LENGTH: 14
<212> TYPE: PRT
<213> ORGANISM: Homo sapiens

<400> SEQUENCE: 21
```

Met Gly Ser Ser Lys Ser Lys Pro Lys Asp Pro Ser Gln Arg
 1               5                  10

```
<210> SEQ ID NO 22
<211> LENGTH: 26
<212> TYPE: PRT
<213> ORGANISM: Homo sapiens

<400> SEQUENCE: 22
```

Leu Leu Gln Arg Leu Phe Ser Arg Gln Asp Cys Cys Gly Asn Cys Ser
 1               5                  10                  15

Asp Ser Glu Glu Glu Leu Pro Thr Arg Leu
            20                  25

```
<210> SEQ ID NO 23
<211> LENGTH: 20
<212> TYPE: PRT
<213> ORGANISM: Rattus norvegicus

<400> SEQUENCE: 23
```

Lys Gln Phe Arg Asn Cys Met Leu Thr Ser Leu Cys Cys Gly Lys Asn
 1               5                  10                  15

Pro Leu Gly Asp
            20

```
<210> SEQ ID NO 24
<211> LENGTH: 19
<212> TYPE: PRT
<213> ORGANISM: Homo sapiens

<400> SEQUENCE: 24
```

Leu Asn Pro Pro Asp Glu Ser Gly Pro Gly Cys Met Ser Cys Lys Cys
 1               5                  10                  15

Val Leu Ser

```
<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: lysomal
      degradation sequence

<400> SEQUENCE: 25
```

```
Lys Phe Glu Arg Gln
 1               5

<210> SEQ ID NO 26
<211> LENGTH: 36
<212> TYPE: PRT
<213> ORGANISM: Cricetulus griseus

<400> SEQUENCE: 26

Met Leu Ile Pro Ile Ala Gly Phe Phe Ala Leu Ala Gly Leu Val Leu
 1               5                  10                  15

Ile Val Leu Ile Ala Tyr Leu Ile Gly Arg Lys Arg Ser His Ala Gly
             20                  25                  30

Tyr Gln Thr Ile
         35

<210> SEQ ID NO 27
<211> LENGTH: 35
<212> TYPE: PRT
<213> ORGANISM: Homo sapiens

<400> SEQUENCE: 27

Leu Val Pro Ile Ala Val Gly Ala Ala Leu Ala Gly Val Leu Ile Leu
 1               5                  10                  15

Val Leu Leu Ala Tyr Phe Ile Gly Leu Lys His His His Ala Gly Tyr
             20                  25                  30

Glu Gln Phe
         35

<210> SEQ ID NO 28
<211> LENGTH: 27
<212> TYPE: PRT
<213> ORGANISM: yeast

<400> SEQUENCE: 28

Met Leu Arg Thr Ser Ser Leu Phe Thr Arg Arg Val Gln Pro Ser Leu
 1               5                  10                  15

Phe Ser Arg Asn Ile Leu Arg Leu Gln Ser Thr
             20                  25

<210> SEQ ID NO 29
<211> LENGTH: 25
<212> TYPE: PRT
<213> ORGANISM: yeast

<400> SEQUENCE: 29

Met Leu Ser Leu Arg Gln Ser Ile Arg Phe Phe Lys Pro Ala Thr Arg
 1               5                  10                  15

Thr Leu Cys Ser Ser Arg Tyr Leu Leu
             20                  25

<210> SEQ ID NO 30
<211> LENGTH: 64
<212> TYPE: PRT
<213> ORGANISM: yeast

<400> SEQUENCE: 30

Met Phe Ser Met Leu Ser Lys Arg Trp Ala Gln Arg Thr Leu Ser Lys
 1               5                  10                  15

Ser Phe Tyr Ser Thr Ala Thr Gly Ala Ala Ser Lys Ser Gly Lys Leu
             20                  25                  30
```

```
Thr Gln Lys Leu Val Thr Ala Gly Val Ala Ala Ala Gly Ile Thr Ala
        35                  40                  45

Ser Thr Leu Leu Tyr Ala Asp Ser Leu Thr Ala Glu Ala Met Thr Ala
    50                  55                  60

<210> SEQ ID NO 31
<211> LENGTH: 41
<212> TYPE: PRT
<213> ORGANISM: yeast

<400> SEQUENCE: 31

Met Lys Ser Phe Ile Thr Arg Asn Lys Thr Ala Ile Leu Ala Thr Val
1               5                   10                  15

Ala Ala Thr Gly Thr Ala Ile Gly Ala Tyr Tyr Tyr Asn Gln Leu
            20                  25                  30

Gln Gln Gln Gln Gln Arg Gly Lys Lys
        35                  40

<210> SEQ ID NO 32
<211> LENGTH: 4
<212> TYPE: PRT
<213> ORGANISM: Artificial Sequence
<220> FEATURE:
<223> OTHER INFORMATION: Description of Artificial Sequence:
      endoplasmic reticulum sequence

<400> SEQUENCE: 32

Lys Asp Glu Leu
1

<210> SEQ ID NO 33
<211> LENGTH: 15
<212> TYPE: PRT
<213> ORGANISM: adenovirus

<400> SEQUENCE: 33

Leu Tyr Leu Ser Arg Arg Ser Phe Ile Asp Glu Lys Lys Met Pro
1               5                   10                  15

<210> SEQ ID NO 34
<211> LENGTH: 19
<212> TYPE: PRT
<213> ORGANISM: Artificial Sequence
<220> FEATURE:
<223> OTHER INFORMATION: Description of Artificial Sequence:
      farnesylation sequence

<400> SEQUENCE: 34

Leu Asn Pro Pro Asp Glu Ser Gly Pro Gly Cys Met Ser Cys Lys Cys
1               5                   10                  15

Val Leu Ser

<210> SEQ ID NO 35
<211> LENGTH: 15
<212> TYPE: PRT
<213> ORGANISM: Artificial Sequence
<220> FEATURE:
<223> OTHER INFORMATION: Description of Artificial Sequence:
      geranylgeranylation sequence

<400> SEQUENCE: 35

Leu Thr Glu Pro Thr Gln Pro Thr Arg Asn Gln Cys Cys Ser Asn
1               5                   10                  15
```

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence:
      destruction sequence

<400> SEQUENCE: 36

Arg Thr Ala Leu Gly Asp Ile Gly Asn
  1               5

<210> SEQ ID NO 37
<211> LENGTH: 20
<212> TYPE: PRT
<213> ORGANISM: Artificial Sequence
<220> FEATURE:
<223> OTHER INFORMATION: Description of Artificial Sequence:  secretory
      sequence

<400> SEQUENCE: 37

Met Tyr Arg Met Gln Leu Leu Ser Cys Ile Ala Leu Ser Leu Ala Leu
  1               5                  10                  15

Val Thr Asn Ser
             20

<210> SEQ ID NO 38
<211> LENGTH: 29
<212> TYPE: PRT
<213> ORGANISM: Artificial Sequence
<220> FEATURE:
<223> OTHER INFORMATION: Description of Artificial Sequence:  secretory
      sequence

<400> SEQUENCE: 38

Met Ala Thr Gly Ser Arg Thr Ser Leu Leu Leu Ala Phe Gly Leu Leu
  1               5                  10                  15

Cys Leu Pro Trp Leu Gln Glu Gly Ser Ala Phe Pro Thr
             20                  25

<210> SEQ ID NO 39
<211> LENGTH: 27
<212> TYPE: PRT
<213> ORGANISM: Artificial Sequence
<220> FEATURE:
<223> OTHER INFORMATION: Description of Artificial Sequence:  secretory
      sequence

<400> SEQUENCE: 39

Met Ala Leu Trp Met Arg Leu Leu Pro Leu Leu Ala Leu Leu Ala Leu
  1               5                  10                  15

Trp Gly Pro Asp Pro Ala Ala Ala Phe Val Asn
             20                  25

<210> SEQ ID NO 40
<211> LENGTH: 18
<212> TYPE: PRT
<213> ORGANISM: Influenza virus

<400> SEQUENCE: 40

Met Lys Ala Lys Leu Leu Val Leu Leu Tyr Ala Phe Val Ala Gly Asp
  1               5                  10                  15

Gln Ile

```
<210> SEQ ID NO 41
<211> LENGTH: 24
<212> TYPE: PRT
<213> ORGANISM: Artificial Sequence
<220> FEATURE:
<223> OTHER INFORMATION: Description of Artificial Sequence:  secretory
      sequence

<400> SEQUENCE: 41

Met Gly Leu Thr Ser Gln Leu Leu Pro Pro Leu Phe Phe Leu Leu Ala
 1               5                  10                  15

Cys Ala Gly Asn Phe Val His Gly
             20

<210> SEQ ID NO 42
<211> LENGTH: 10
<212> TYPE: PRT
<213> ORGANISM: Artificial Sequence
<220> FEATURE:
<221> NAME/KEY: UNSURE
<222> LOCATION: (3)..(6)
<223> OTHER INFORMATION: Xaa at positions 3 through 6 can be any amino
      acid.
<223> OTHER INFORMATION: Description of Artificial Sequence:  stability
      sequence

<400> SEQUENCE: 42

Met Gly Xaa Xaa Xaa Xaa Gly Gly Pro Pro
 1               5                  10

<210> SEQ ID NO 43
<211> LENGTH: 5
<212> TYPE: PRT
<213> ORGANISM: Artificial Sequence
<220> FEATURE:
<223> OTHER INFORMATION: Description of Artificial Sequence:  linker
      sequence

<400> SEQUENCE: 43

Gly Ser Gly Gly Ser
 1               5

<210> SEQ ID NO 44
<211> LENGTH: 4
<212> TYPE: PRT
<213> ORGANISM: Artificial Sequence
<220> FEATURE:
<223> OTHER INFORMATION: Description of Artificial Sequence:  linker
      sequence

<400> SEQUENCE: 44

Gly Gly Gly Ser
 1

<210> SEQ ID NO 45
<211> LENGTH: 39
<212> TYPE: PRT
<213> ORGANISM: Artificial Sequence
<220> FEATURE:
<221> NAME/KEY: UNSURE
<222> LOCATION: (11)..(28)
<223> OTHER INFORMATION: Xaa at positions 11 through 28 can be any amino
      acid.
<223> OTHER INFORMATION: Description of Artificial Sequence:  Synthetic

<400> SEQUENCE: 45

Met Gly Glu Phe Leu Ile Val Ile Lys Ser Xaa Xaa Xaa Xaa Xaa Xaa
 1               5                  10                  15
```

```
Xaa Xaa Xaa Xaa Xaa Xaa Xaa Xaa Xaa Xaa Xaa Xaa Glu Phe Leu Ile
                20                  25                  30

Val Ile Lys Ser Gly Pro Pro
             35

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence:  Synthetic

<400> SEQUENCE: 46

Phe Leu Ile Val Ile Lys Ser
 1               5

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence:  Synthetic

<400> SEQUENCE: 47

Ser Lys Val Ile Leu Phe Glu
 1               5

<210> SEQ ID NO 48
<211> LENGTH: 114
<212> TYPE: PRT
<213> ORGANISM: Artificial Sequence
<220> FEATURE:
<223> OTHER INFORMATION: Description of Artificial Sequence:  Synthetic

<400> SEQUENCE: 48

Gly Ala Thr Cys Cys Cys Ala Cys Cys Ala Cys Ala Thr Gly Gly
 1               5                  10                  15

Gly Cys Gly Ala Gly Thr Thr Cys Thr Thr Gly Ala Thr Cys Gly Thr
                 20                  25                  30

Gly Ala Ala Gly Thr Cys Ala Gly Gly Asn Asn Lys Asn Asn Lys
             35                  40                  45

Asn Asn Lys Asn Asn Lys Asn Asn Lys Asn Asn Lys Asn Asn Lys Asn
     50                  55                  60

Asn Lys Asn Asn Lys Asn Asn Lys Asn Asn Lys Asn Asn Lys Asn Asn
 65                  70                  75                  80

Lys Asn Asn Lys Asn Asn Lys Asn Asn Lys Asn Asn Lys Asn Asn Lys
                 85                  90                  95

Gly Gly Ala Gly Ala Ala Thr Thr Cys Cys Thr Thr Ala Thr Cys Gly
             100                 105                 110

Thr Cys

<210> SEQ ID NO 49
<211> LENGTH: 62
<212> TYPE: PRT
<213> ORGANISM: Artificial Sequence
<220> FEATURE:
<223> OTHER INFORMATION: Description of Artificial Sequence:  Synthetic

<400> SEQUENCE: 49

Gly Ala Thr Cys Cys Cys Ala Ala Thr Thr Ala Ala Thr Gly Gly
 1               5                  10                  15

Gly Ala Ala Thr Cys Ala Gly Gly Thr Thr Thr Thr Ala Ala Gly Gly
```

```
                    20                  25                  30

Ala Gly Gly Cys Cys Cys Thr Gly Ala Thr Thr Thr Gly Ala Cys Gly
            35                  40                  45

Ala Thr Ala Ala Gly Gly Ala Ala Thr Thr Cys Thr Cys Cys
        50                  55                  60

<210> SEQ ID NO 50
<211> LENGTH: 40
<212> TYPE: PRT
<213> ORGANISM: Artificial Sequence
<220> FEATURE:
<223> OTHER INFORMATION: Description of Artificial Sequence:  Synthetic

<400> SEQUENCE: 50

Met Gly Glu Phe Leu Ile Val Lys Val Trp Gly Arg Met Val Cys Trp
 1               5                  10                  15

Val Leu Val Val Arg Arg Phe Val Leu Val Ile Val Leu Glu Asn Ser
            20                  25                  30

Leu Ser Ser Asn Gln Gly Pro Pro
        35                  40

<210> SEQ ID NO 51
<211> LENGTH: 39
<212> TYPE: PRT
<213> ORGANISM: Artificial Sequence
<220> FEATURE:
<223> OTHER INFORMATION: Description of Artificial Sequence:  Synthetic

<400> SEQUENCE: 51

Met Gly Glu Phe Leu Ile Val Lys Ser Gly His Ser Ser Gly Ile Pro
 1               5                  10                  15

Val Gly Val Gly Trp Cys Trp Asn Ser Ala Gly Gly Gly Glu Phe Leu
            20                  25                  30

Ile Val Lys Ser Gly Pro Pro
        35
```

METHODS OF SCREENING FOR A MULTI-DRUG RESISTANCE CONFERRING PEPTIDE

This application claims the benefit of Provisional application Ser. No. 60/136,018 filed May 25, 1999.

FIELD OF THE INVENTION

The invention relates generally to methods of screening for agents which bind to and/or regulate cellular proteins involved in drug resistance, particularly resistance of tumor cells to chemotherapeutic agents.

BACKGROUND OF THE INVENTION

Biochemical and genetic approaches are commonly used to identify key aspects of signaling pathways involved in a pathological phenotype. Biochemical approaches characterize intracellular protein components, whereas genetic approaches characterize mutations in cellular components. Pharmacology has long complemented genetic and biochemical approaches by identifying candidate agents that bind to a component of interest. Although candidate agents can be any molecule, they are typically small organic compounds. Small organic compounds often affect polypeptide structure, stability, or function. Additionally, small organic compounds can influence the manner in which proteins interact with each other (Fabbrizio, E., et al., (1999) *Oncogene*, 18:4357–63). This in trans effector function of small organic molecules offers subtle means by which signaling pathways can be studied or corrected.

Screening molecular libraries of chemical compounds for trans-effector molecules provides another means by which signaling pathways can be characterized. It should be possible to deliver to cells libraries of diverse organic molecules in the form of small peptides. Peptides have been used in in vitro library screens against known target proteins (Wong, D. W. & Robertson, G. H., (1998) *Ann. N. Y. Acad. Sci*., 864, 555–557; Bremnes, T., et al.,.(1998) *Immunotechnology*, 4, 21–8). Peptide libraries expressed in phage have been used to isolate high affinity aptamers that bind to known target molecules. Such binding can be shown to influence protein function in vitro. Chemically synthesized libraries of peptides also have been made and screened in a variety of in vitro assays with similar levels of efficacy. However, it has not been possible, to screen peptides against entire pathways within living cells.

An approach based on screening peptides against entire pathways requires knowledge of the stimulus that activates the disease and a phenotypic outcome. For instance, the stimulus can be environmentally determined, such as the response to a cytokine, or can be constitutively present, such as a mutated protein that continuously signals a mitogenic response leading to an oncogenic phenotype. The phenotypic outcome can be considered movement towards, or away from, the disease state using as a genetic selection tool any of a number of surrogate indicators of phenotype. The closest attempts at such are screens of cDNA libraries for complementation in mammalian cells.

It would be particularly valuable to screen for peptides against pathways which lead to the loss of sensitivity to chemotherapeutic drugs in tumor cells. The loss of sensitivity to chemotherapeutic drugs results in resistance to multiple chemotherapeutic drugs. This resistance is termed multi-drug resistance (MDR) and arises with a variety of therapeutic agents in a wide range of malignancies. Multiple drug resistance, and hence tumor cell selection, outgrowth, and relapse, leads to morbidity and mortality in cancer patients.

One mechanism used by tumor cells to acquire MDR is up-regulation of P-glycoprotein (P-gp), the product of the MDR-1 gene. Such upregulation is associated with the MDR phenotype of many human cancers, including a wide variety of solid tumors (Kaye, S. B., (1998) *Curr. Opin. Oncol.*, 10 Suppl 1, S15–19) and certain leukemias and lymphomas (Hart, S. M. et al, (1993) *Leuk Lymphoma*, 11, 239–248; Yamaguchi, M. et al., (1995) *Cancer*, 76, 2351–2356). P-gp is a transmembrane protein that functions as an energy-dependent efflux pump whose normal function is to transport metabolites and to provide protection against cytotoxic substances (Bello-Reuss, E. & Ernest, S., (1994) *Am. J. Physiol.*, 267, C1351–1358; Chin, K. V., et al., (1990) *Cell Growth Differ.*, 8, 361–365). Over-expression of P-gp results in the expulsion of intracellular anticancer drugs and the consequent establishment of resistance to those compounds. Such drug resistance has been demonstrated in tumor cells upon exposure to cytotoxic drugs such as Taxol (Parekh, H., Wiesen, K. & Simpkins, H. (1997) *Biochem. Pharmacol.*, 53, 461–470), as well as with many other chemotherapeutic agents (Fardel, O., et al., (1994) *Eur. J. Biochem.*, 219, 521–528). Other proteins implicated in MDR are regulators of apoptosis (i.e., Bcl-2 and Bcl-xL) and LRP (lung resistance protein). The LRP protein has been implicated in multidrug resistance in ovarian carcinoma, metastatic malignant melanoma, and acute myeloid leukemia (Leith, C., (1998) *Curr. Opin. Hematol.*, 5, 287–291).

Accordingly, the cellular components involved in rendering cells resistant to chemotherapy is of paramount interest, and it is an object of the invention to provide proteins and related molecules involved in MDR. It is a further object of the invention to provide recombinant nucleic acids involved in MDR, and expression vectors and host cells containing the nucleic acid encoding proteins involved in MDR. A further object of the invention is to provide methods for screening for antagonists and agonists of proteins involved in MD.

SUMMARY OF THE INVENTION

In accordance with the objects outlined above, the present invention provides methods and compositions for screening for agents that confer or ameliorate MDR. Accordingly, the invention provides bioactive agent, such as resistance conferring peptides that confer a MDR phenotype and drug candidates that ameliorate the MDR phenotype.

In one aspect, the invention provides methods for screening for bioactive agents that confer multi-drug resistance on a cell. The methods comprise the steps of a) introducing a retroviral library of randomized candidate peptide into a plurality of cells, wherein each of said peptides comprises a different peptide sequence; b) screening the plurality of cells for a 6 cell exhibiting a MDR phenotype, wherein the MDR phenotype is due to the presence of a bioactive agent. The methods may also include the steps of c) isolating the cell(s) exhibiting the MDR phenotype; and, d) isolating a resistance conferring peptide from the cell(s).

The invention further provides methods for isolating a protein of a resistance pathway.

In a further aspect, the invention provides methods for screening for a bioactive agent capable of binding a protein of a multi-drug resistance pathway. The methods comprise the steps of a) combining a protein of a multi-drug resistance pathway and a candidate bioactive agent; and b) determining the binding of the candidate agent to the protein.

The invention further provides methods of identifying a drug candidate comprising the steps of a) contacting a protein of a multi-drug resistance pathway and a resistance conferring peptide; and b) detecting a decrease in the binding of the peptide to the protein in the presence of the candidate drug, thereby identifying a drug candidate.

In a further aspect, the invention provides methods for identifying a bioactive agent capable of modulating, the activity of a protein of a multi-drug resistance pathway. The methods comprise the steps of a) adding a candidate bioactive agent to a plurality of cells, wherein each of said cells expresses a protein of a multi-drug resistance pathway; b) adding a chemotherapeutic agent to said plurality; and c) determining the effect of the candidate bioactive agent on resistance to the chemotherapeutic agent.

In an additional aspect, the present invention provides methods of treating a multidrug resistance associated disease comprising administering compositions of modulators of proteins of multi-drug resistance pathway.

BRIEF DESCRIPTION OF THE DRAWINGS

FIG. 1 depicts a screen for peptides conferring taxol resistance to HeLa cells. FIG. 1A illustrates the peptide library screen. The vector shown at the top of the diagram encodes a single long terminal repeat (LTR)-driven RNA transcript encoding an operon capable of co-expressing a peptide and the GFP indicator gene. The translation of the GFP is initiated from the internal ribosomal entry site (IRES). ψ represents the viral packaging sequence. To initiate a screen a peptide library (complexity $3 \times 10^8$) encoded within the vector is transfected into the viral packaging cell line Phoenix-ampho. The viral particles are harvested and then used to transduce HeLa cells. The infected HeLa cells are treated with a lethal dose of Taxol. The peptide sequences are rescued from surviving clones by RT-PCR and then recloned into a Tet-regulatable (Tra) retroviral vector. The Tra vector contains the tetracycline-responsive element (TRE), minimal immediate early promoter of cytomegalovirus (Pmin) and 3' SIN-LTR which has removed the promoter and enhancer function and allow the transcription is driven by TRE/Pmin. The effect of these peptides on Taxol resistance is then re-tested on naive HeLa cells. After confirming the Taxol resistant phenotype, the cellular target of these peptides are isolated by yeast two-hybrid screening. The functions of these cellular proteins in Taxol resistance are then further validated.

FIG. 1B depicts enhanced survival of HeLa cells infected with the peptide RGP8.5 in a clonogenic survival assay. HeLa cells were infected with a tet-regulatory retroviral vector (Tra) expressing the RGP8.5 peptide or GFP control. After infection, $2 \times 10^5$ cells were split into one well of 6-well plate and half of cells were incubated with Dox. The next day the cells were treated with different dosages of Taxol for 48 hours. Two weeks later, the surviving colonies were stained with Giemsa solution and photographed. The cells with Dox were kept in Dox throughout the experiment. This assay has been repeated with the RGP8.5 peptide several times. Similar results were obtained (data not shown).

FIG. 2 demonstrates that the RGP8.5 peptide upregulates MDR1 in HeLa cells. FIG. 2A shows Taxol resistant HeLa cells expressing the RGP8.5 peptide. HeLa cells infected with different retroviral vectors, stained with monoclonal antibody MDR1 (UIC2) PE conjugate and analyzed on a fluorescence-activated cell sorting (FACS) machine. The upper left panel shows cells expressing the GFP control vector with GFP expression on the X axis and MDR expression on the Y axis. The middle left panel is the 8.2 peptide control showing no effect upon MDR expression. Bottom left is the 8.5 pool that shows significant expression of MDR correlated to GFP expression (surrogate indicator of peptide). The right hand panels verify that the selected clone RGP8.5.1 regulates MDR expression according to induced vector expression. Upper right is the HeLa control; middle right is vector expression in absence of presumed peptide expression; lower right is after derepression of peptide expression showing induced MDR expression correlating with GFP (peptide) expression.

FIG. 2B depicts Taxol resistance after derepression of vector induction in HeLa cells. Cells expressing the RGP8.5 peptide (selected clone) were incubated with or without 200 ng/ml Dox for 2 days. Subsequently, the cells were incubated with 100 nM Taxol for 48 hours and then visualized for cell survival.

FIG. 2C depicts inhibition of MDR-1 pump activity by CsA antagonizes RGP8.5 peptide activity. The cells with Dox were first incubated with doxycycline for 2 days before seeding in 96-well plates. After that point the cells were kept in medium with Dox for the entire experimental period. $5 \times 10^3$ cells were split in one well of a 96-well plate. The next day the cells were treated with different concentrations of Taxol plus or minus 2 $\mu$M CsA in combination with Dox. Data presented are the mean values of each treatment in triplicate in a standard XTT assay. Error bars were smaller than graph data points and are therefore not observable in the Figure. Experimental samples are as indicated in the graph inset.

FIG. 2D depicts a Rhodamine 123 efflux assay of a RGP8.5 expressing HeLa clone. Cells were incubated with or without 200 ng/ml Dox for 4 days. Subsequently the cells were stained with 1 nM Rhodamine 123 and analyzed on FACS. In the top panels the GFP positive cells (striped peak, top left) were seen to extrude Rhodamine 123 from cells (striped peak, top right). Cells that did not activate the GFP did not activate pump activity (solid black). The bottom two panels show cells in which the tTA promoter was shut down in the presence of Dox. Most cells were below GFP threshold and showed strong retention of Rhodamine 123 (solid black peak).

FIG. 3 depicts RT-PCR analysis of mdr1 mRNA expression of a HeLa clone expressing RGP8.5 peptide. Total RNA from RGP8.5.1 was isolated and equal amounts of RNA were used to do semi-quantitative RT-PCR (25 cycles). The HeLa clone was first incubated with doxycycline 200 ng/ml for 0, 4, 8, 12 hours (lanes 1, 2, 3, and 4) and 3 days (lane 5) before harvesting to purify RNA. Equal amount of RT products were used in the mdr1 and β-tubulin PCR amplifications.

FIG. 4 depicts immunoprecipitation and western blot anaysis of the association of RGP8.5 peptide with XAPC7 and Zeta proteins. FIG. 4A depicts the association of expressed RGP8.5 in cells with proteasome subunits. The plasmids encoded GFP-RGP8.5 (lanes 1, 2 and 3) and GFP-RGP56.1 fusions (lanes 4, 5 and 6) were contransfected with vector alone (lanes 1 and 4), flag tagged Zeta (lanes 2 and 5) and XAPC7 (lanes 3 and 6) expression vector into HeLa cells. Forty eight hours post-transfection, the cells were harvested, lysed in TNT buffer and subjected to immunoprecipitation with anti-flag antibody bearing beads. The co-precipitated proteins were separated in SDS-PAGE and detected with anti-GFP antibody. For detection of the expression of GFP-peptide fusions, Zeta and XAPC7, an equal amount of cell extracts was loaded on the gel and the protein expression was revealed with antibodies against GFP and flag tag.

FIG. 4B shows purification of proteasome subunits using an RGP8.5 affinity column. HeLa cell extract were pre-cleared with a streptavidin column. The biotinylated RG8.5 peptide was then added to the cell lysate and allowed to mix overnight at 4° C. Next day streptavidin agarose beads were incubated with the cell extract for 3 hours at 4° C. After washing the beads five times with lysis buffer, the associated proteins were eluted with 2× protein sample buffer, resolved on SDS-PAGE and detected with monoclonal antibody against Zeta and XAPC7 proteasome subunits.

FIG. 5 depicts phenocopying peptide expression by proxy inhibition of the proteasome induces MDR-1 expression. FIG. 5A shows RT-PCR analysis of mdr1 mRNA expression of a HeLa clone expressing RGP8.5 peptide. The total RNA of HeLa cells (lane 1) and the RGP8.5 HeLa clone (lanes 2, 3 and 4) were isolated and equal amount of RNA were used to do RT-PCR (25 cycles). The HeLa clone was first incubated with doxycycline 200 ng/ml (lane 3) plus 5 μM MG132 (Lane 4) for 23 hour before harvesting cells for RNA preparation. Equal amounts of RT products were used in mdr1 and β-tubulin PCR amplification.

FIG. 5B shows inhibition of the proteasome by MG132 induces MDR-1 protein expression. The RGP8.5 peptide-expressing clone was incubated with or without 200 ng/ml Dox for 2 days and subsequently cells were treated with or without 5 μM MG132 for 21 hours. The cells were stained with monoclonal antibody MDR1 (UIC2) PE conjugate and analyzed on FACS.

FIG. 6 depicts that inhibition of proteasome activity by RGP8.5 arrests cell cycle progression. FIG. 6A shows a Western blot analysis of endogenous levels of GFP, hsp70 and cyclin B proteins in HeLa clones expressing RGP8.5 peptide. To examine the effect of RGP8.5 on the endogenous protein expression, RGP8.5 expressing HeLa cells were incubated with doxycycline (200 ng/ml) for 4 days before harvesting for western analysis. Equal amount of cell lysate were loaded on each lane, separated by SDS-PAGE and immunoblotted with antiserum against GFP (Kodak), hsp70 and cyclin B1 (Santa Cruz).

FIG. 6B shows cell cycle analysis of RG8.5 peptide expressing cells. RG8.5 peptide expressing cells were growing to 50% confluence. The cells were harvested and processed for flow cytometry of DNA. In the DNA content profile, the bold line represents the peptide negative cells and the grayed area curve represents the RG8.5 peptide positive cells. Cells were gated for GFP expression, FIG. 6B top, as indicated.

FIG. 7A depicts the amino acid sequence of RGP8.5 (SEQUENCE ID NO: 1) and FIG. 7B the nucleotide sequence of RGP8.5 (SEQUENCE ID NO:2).

FIG. 8A depicts the nucleotide sequence of proteasome subunit XAPC7 (SEQUENCE ID NO: 3; Genbank Accession No. AFO22815). FIG. 8B depicts the amino acid sequence of proteasome subunit XPAC7 (SEQUENCE ID NO: 4, Genbank Accession No. AAB81515). See Huang, J., et al., (1996) *J. Virol.*, 70:5582–5591. FIG. 8C depicts the depicts the nucleotide sequence of proteasome subunit Zeta (SEQUENCE ID NO: 5, genbank Accession No. NM_002790). FIG. 8D depicts the amino acid sequence of proteasome subunit Zeta (SEQUENCE ID NO: 6, Genbank Accession No. NP_002781. See DeMartinio, G. N., et al., (1991) *Biochim. Biophys. Acta*, 1079:29038).

DETAILED DESCRIPTION OF THE INVENTION

The present invention provides methods of identifying candidate agents that bind to and regulate cellular proteins involved in multi-drug resistance (MDR). As outlined herein, there are two basic types of screens that can be done: 1) screens for compounds that confer a multidrug resistance phenotype; and, 2) screens for compounds that ameliorate a multidrug resistance phenotype.

Accordingly, in a preferred embodiment, libraries of candidate agents are used to screen for compounds that confer a multidrug resistance phenotype. The target molecules of the compounds are identified; and in the presence of the compounds are used to screen libraries of candidate drugs that bind to the target molecules and/or modulate their activity. For example, as outlined herein compounds, such as the RGP8.5 peptide that confers an MDR phenotype, are used to identify target molecules within an MDR pathway. Once target molecules have been identified, as is outlined herein with the identification of XAPC7 and Zeta, and, when inhibited by the RGP8.5 peptide confer multidrug resistance, the XAPC7 and Zeta molecules can be used in screens for candidate drugs that bind to them and modulate their activity.

Accordingly, the disclosed methods use genetic screens to identify proteins of multi-drug resistance pathways (i.e: PRP proteins, defined below), which render cells resistant to chemotherapeutics such as Taxol, Etoposide, Cisplatin, and others. Also provided are methods for the identification and isolation of PRP proteins, the tools to characterize pathways of resistance, and methods of screening for candidate bioactive agents capable of binding to and modulating the activity of PRP proteins to identify new drugs that can be used to treat MDR.

The present invention provides methods for the screening of candidate bioactive agents which confer resistance to a chemotherapeutic drug. These "resistance conferring" agents are capable of binding to a cellular protein that causes or at least contributes to cell death upon exposure to a chemotherapeutic agent. Thus, a resistance conferring agent interacts or modulates a protein of a resistance pathway (PRP protein, see below), thereby inducing resistance to a chemotherapeutic agent(s). By delivering random peptides or oligonucleotides to cells, placing these cells under selection pressure using a chemotherapeutic drug, and harvesting those cells which survive, the agent responsible for cell survival is identified. In addition, the present methods allow for identification of the cellular protein to which the agent binds, and the subsequent use of that cellular protein in screens for bioactive agents, i.e., sensitizing agents, which can be used to alleviate the MDR phenotype.

Using these methods, a resistance conferring peptide, RGP8.5 and two PRP proteins, XAPC7 and Zeta, have been identified. See also U.S. Ser. No. 60/136,018, hereby expressly incorporated by reference.

XAPC7 and Zeta are α type proteasome subunits (Groettrup & Schmidtke, (1999) *Drug discovery Today*, 4:63–71). The proteasome is the major system for bulk degradation of proteins in the cell. Key biological processes controlled by the proteasome include cell-cycle regulation, apoptosis, morphogenesis, differentiation, metabolic control and antigen presentation (Groettrup & Schmidtke, I; Chen, Z. et al., (1995) *Genes Dev.*, 9, 1586–1597; Tsurumi, C., et al., (1996) *Nippon Rinsho*, 54, 861–869). The 20S proteasome is a barrel-shaped core proteolytic complex consisting of four rings with seven subunits each. Subunits of the inner two rings are of the beta type and bear the proteolytically active centers pointing towards the lumen of the barrel; the outer two rings are of the alpha type and control access to the inner chambers of the proteasome and association with regulatory complexes (Groettrup, M. & Schmidtke, G., (1999) *Drug Research*, 4, 63–71; Kania, M. A., et al., (1996) *Eur. J. Biochem.*, 236, 510–516).

Drugs that inhibit proteasome activity have been shown to affect cell cycle progression. Many cell cycle regulatory factors such as p21 and cyclinB are extremely unstable, with rapidly varying intracellular levels that are controlled by proteasome-mediated proteolytic degradation during the cell cycle. The degradation of cyclinB by the 26S proteasome is required for the cell cycle transition from metaphase to anaphase (Spataro, V., et al., (1997) *J. Biol. Chem.*, 272:30470–5).

The resistance conferring peptide, RGP8.5 upregulates MDR-1 expression, see Examples below. Without being bound by theory, RGP8.5 may bind to XPAC7 and interfere with proteasome activity. This theory is supported by the observation that the Hepatitis B virus pX protein (X factor) has been shown to transactivate the MDR1 gene (Doong, S. L. et al., (1998) *J. Hepatol.*, 29, 872–878). XAPC7 associates with X factor in a yeast two-hybrid protein interaction screening and antisense expression of XAPC7 leads to blocked transactivation by X factor (Huang, J., et al., (1996) *J. Virol.* 70, 5582–5591; Jorgensen, L. & Hendil, K. B. (1999) *Mol. Biol. Rep.* 26,119–123).

The Zeta subunit has been suggested as a putative ribonuclease and may regulare mRNA expression by acting on a protein bound to constitutively expressed transcripts of mdr-1 (Fischer, M., Runkel, L. & Schaller, H., (1995) *Virus Genes*, 10, 99–102; Petit, F. et al., (1997) *Biochem. J.*, 326, 93–98). Thus, the RGP8.5 peptide may confer resistance to the chemotherapeutic drug Taxol by acting as a proteasome inhibitor.

Therefore, without being bound by theory, one form of drug resistance in cancer cells may arise through mutation or modification of the XPAC7 or Zeta proteasome alpha subunits or their specificity of action. Changes in how the proteasome degrades target molecules could directly affect regulators of MDR-1 protein production and lead to up-regulation of MDR-1 and a chemotherapeutic resistance state.

The XAPC7 and Zeta proteins have thus been identified as playing a role in MDR, and can been used in a variety of methods, including screening candidate drugs for selective modulation of XAPC7 and/or Zeta activity.

Proteins, such as XAPC7 and Zeta, which play a role in MDR are defined herein as "proteins of resistant pathways" or "PRP proteins". Thus, PRP proteins are cellular components involved in rendering cells resistant to chemotherapy.

Accordingly, the present invention provides methods for screening candidate bioactive agents for a moiety capable of binding to or modulating the activity of a PRP protein such as XAPC7 and Zeta.

The term "candidate bioactive agent" or "candidate drug" or "exogeneous compound" as used herein describes any molecule, e.g., protein, small organic molecule, carbohydrates (including polysaccharides), polynucleotide, lipids, etc. Generally a plurality of assay mixtures are run in parallel with different agent concentrations to obtain a differential response to the various concentrations. Typically, one of these concentrations serves as a negative control, i.e., at zero concentration or below the level of detection. In addition, positive controls can be used.

Candidate agents encompass numerous chemical classes, though typically they are organic molecules, preferably small organic compounds having a molecular weight of more than 100 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Particularly preferred are peptides.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed; or random chemical modifications, such as acylation, alkylation, esterification, amidification to produce structural analogs.

In a preferred embodiment, the candidate bioactive agents are proteins. By "protein" herein is meant at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and noreleucine are considered amino acids for the purposes of the invention. "Amino acid" also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations. Chemical blocking groups or other chemical substituents may also be added.

In a preferred embodiment, the candidate bioactive agents are naturally occurring proteins or fragments of naturally occurring proteins. Thus, for example, cellular extracts containing proteins, or random or directed digests of proteinaceous cellular extracts, may be used. In this way libraries of procaryotic and eukaryotic proteins may be made for screening in the systems described herein. Particularly preferred in this embodiment are libraries of bacterial, fungal, viral, and mammalian proteins, with the latter being preferred, and human proteins being especially preferred.

In a preferred embodiment, the candidate bioactive agents are peptides of from about 5 to about 30 amino acids, with from about 5 to about 20 amino acids being preferred, and from about 7 to about 15 being particularly preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In a preferred embodiment, the candidate bioactive agents are nucleic acids. By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage, et al., Tetrahedron, 49(10):1925 (1993) and references therein; Letsinger, J. Org. Chem., 35:3800 (1970); Sprinzl, et al., Eur. J. Biochem., 81:579(1977); Letsinger, et al., Nucl. Acids Res., 14:3487(1986); Sawai, et al., Chem. Lett., 805 (1984), Letsinger, et al., J. Am. Chem. Soc., 110:4470 (1988); and Pauwels, et al., Chemica Scripta, 26:141 (1986)), phosphorothioate (Mag, et al., Nucleic Acids Res., 19:1437 (1991); and U.S. Pat. No. 5,644,048), phosphorodithioate (Briu, et al., J. Am. Chem. Soc., 111:2321 (1989)), O-methylphophoroamidite linkages (see Eckstein, Oligonucleotides and Analogues: A Practical Approach, Oxford University Press), and peptide nucleic acid backbones and linkages (see Egholm, J. Am. Chem. Soc., 114:1895 (1992); Meier, et al., Chem. Int. Ed. Engl., 31:1008 (1992); Nielsen, Nature, 365:566 (1993); Carlsson, et al., Nature, 380:207 (1996), all of which are incorporated by reference)). Other analog nucleic acids include those with positive backbones (Denpcy, et a., Proc. Natl. Acad. Sci. USA, 92:6097 (1995)); non-ionic backbones (U.S. Pat. Nos. 5,386,023; 5,637,684; 5,602,240; 5,216,141; and 4,469,863; Kiedrowshi, et al., Angew. Chem. Intl. Ed. English, 30:423 (1991); Letsinger, et al., J. Am. Chem. Soc., 110:4470 (1988); Letsinger, et al., Nucleoside & Nucleotide, 13:1597 (1994); Chapters 2 and 3, ASC Symposium Series 580, "Carbohydrate Modifications in Antisense Research", Ed. Y. S. Sanghui and P. Dan Cook; Mesmaeker, et al., Bioorganic & Medicinal Chem. Lett., 4:395 (1994); Jeffs, et al., J. Biomolecular NMR, 34:17 (1994); Tetrahedron Lett., 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins, et al., Chem. Soc. Rev., (1995) pp. 169–176). Several nucleic acid analogs are described in Rawls, C & E News, Jun. 2, 1997, page 35. All of these references are hereby expressly incorporated by reference. These modifications of the ribose-phosphate backbone may be done to facilitate the addition of additional moieties such as labels, or to increase the stability and half-life of such molecules in physiological environments. In addition, mixtures of naturally occurring nucleic acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

As described above generally for proteins, nucleic acid candidate bioactive agents may be naturally occurring nucleic acids, random nucleic acids, or "biased" random nucleic acids. For example, digests of procaryotic or eukaryotic genomes may be used as is outlined above for proteins.

In a preferred embodiment, the candidate bioactive agents are organic chemical moieties, a wide variety of which are available in the literature.

In a preferred embodiment, a library of different candidate bioactive agents are used. Preferably, the library should provide a sufficiently structurally diverse population of randomized agents to effect a probabilistically sufficient range of diversity to allow binding to a particular target. Accordingly, an interaction library should be large enough so that at least one of its members will have a structure that gives it affinity for the target. Although it is difficult to gauge the required absolute size of an interaction library, nature provides a hint with the immune response: a diversity of $10^7$–$10^8$ different antibodies provides at least one combination with sufficient affinity to interact with most potential antigens faced by an organism. Published in vitro selection techniques have also shown that a library size of $10^7$ to $10^8$ is sufficient to find structures with affinity for the target. A library of all combinations of a peptide 7 to 20 amino acids in length, such as generally proposed herein, has the potential to code for $20^7$ ($10^9$) to $20^{20}$. Thus, with libraries of $10^7$ to $10^8$ different molecules the present methods allow a "working" subset of a theoretically complete interaction library for 7 amino acids, and a subset of shapes for the $20^{20}$ library. Thus, in a preferred embodiment, at least $10^6$, preferably at least $10^7$, more preferably at least $10^8$ and most preferably at least $10^9$ different sequences are simultaneously analyzed in the subject methods. Preferred methods maximize library size and diversity.

The candidate bioactive agents are combined or added to a cell or population of cells. Suitable cell types for different embodiments are outlined above. The candidate bioactive agent and the cells are combined. As will be appreciated by those in the art, this may accomplished in any number of ways, including adding the candidate agents to the surface of the cells, to the media containing the cells, or to a surface on which the cells are growing or in contact with; adding the agents into the cells, for example by using vectors that will introduce the agents into the cells (i.e. when the agents are nucleic acids or proteins).

In a preferred embodiment, the candidate bioactive agents are either nucleic acids or proteins (proteins in this context includes proteins, oligopeptides, and peptides) that are introduced into the host cells using vectors, including viral vectors. The choice of the vector, preferably a viral vector, will depend on the cell type. When the cells are replicating, retroviral vectors are used as is more fully described below. When the cells are not replicating (i.e. they are arrested in one of the growth phases), other viral vectors may be used, including lentiviral and adenoviral vectors.

In a preferred embodiment, the cells are either replicating or can be induced to replicate, and retroviral vectors are used to introduce candidate bioactive agents to the cells, as is generally outlined in PCT US97/01019 and PCT US97/01048, both of which are expressly incorporated by reference. Generally, a library of retroviral vectors is made using retroviral packaging cell lines that are helper-defective and are capable of producing all the necessary trans proteins, including gag, pol and env, and RNA molecules that have in cis the ψ packaging signal. Briefly, the library is generated in a retrovirus DNA construct backbone; standard oligonucleotide synthesis is done to generate either the candidate agent or nucleic acid encoding a protein, for example a random peptide, using techniques well known in the art. After generation of the DNA library, the library is cloned into a first primer. The first primer serves as a "cassette", which is inserted into the retroviral construct. The first primer generally contains a number of elements, including for example, the required regulatory sequences (e.g. translation, transcription, promoters, etc), fusion partners, restriction endonuclease (cloning and subcloning) sites, stop codons (preferably in all three frames), regions of complementarity for second strand priming (preferably at the end of the stop codon region as minor deletions or insertions may occur in the random region), etc.

A second primer is then added, which generally consists of some or all of the complementarity region to prime the first primer and optional necessary sequences for a second unique restriction site for subcloning. DNA polymerase is added to make double-stranded oligonucleotides. The double-stranded oligonucleotides are cleaved with the appropriate subcloning restriction endonucleases and subcloned into the target retroviral vectors, described below.

Any number of suitable retroviral vectors may be used. Generally, the retroviral vectors may include: selectable marker genes as is more fully described below; promoters driving expression of a second gene, placed in sense or anti-sense relative to the 5' LTR; CRU5 (a synthetic LTR), tetracycline regulation elements in SIN, cell specific promoters, etc.

Preferred retroviral vectors include a vector based on the murine stem cell virus (MSCV) (see Hawley et al., Gene Therapy 1:136 (1994)) and a modified MFG virus (Rivere et al., Genetics 92:6733 (1995)), and pBABE, outlined in PCT US97/01019.

The retroviruses may include inducible and constitutive promoters for the expression of the candidate agent. For example, there are situations wherein it is necessary to induce peptide expression only during certain phases of the selection process, or only in certain cell phases (i.e. using phase specific promoters, such as E2F responsive promoter, p53 responsive promoter, cyclin promoters, etc.). A large number of both inducible and constitutive promoters are known.

In addition, it is possible to configure a retroviral vector to allow inducible expression of retroviral inserts after integration of a single vector in target cells; importantly, the entire system is contained within the single retrovirus. Tet-inducible retroviruses have been designed incorporating the Self-Inactivating (SIN) feature of 3' LTR enhancer/promoter retroviral deletion mutant (Hoffman et al., PNAS USA 93:5185 (1996)). Expression of this vector in cells is virtually undetectable in the presence of tetracycline or other active analogs. However, in the absence of Tet, expression is turned on to maximum within 48 hours after induction, with uniform increased expression of the whole population of cells that harbor the inducible retrovirus, indicating that expression is regulated uniformly within the infected cell population. A similar, related system uses a mutated Tet DNA-binding domain such that it bound DNA in the presence of Tet, and was removed in the absence of Tet. Either of these systems is suitable.

In a preferred embodiment, the candidate bioactive agents are linked to a fusion partner. By "fusion partner" or "functional group" herein is meant a sequence that is associated with the candidate bioactive agent, that confers upon all members of the library in that class a common function or ability. Fusion partners can be heterologous (i.e. not native to the host cell), or synthetic (not native to any cell). Suitable fusion partners include, but are not limited to: a) presentation structures, as defined below, which provide the candidate bioactive agents in a conformationally restricted or stable form; b) targeting sequences, defined below, which allow the localization of the candidate bioactive agent into a subcellular or extracellular compartment; c) rescue sequences as defined below, which allow the purification or isolation of either the candidate bioactive agents or the nucleic acids encoding them; d) stability sequences, which confer stability or protection from degradation to the candidate bioactive agent or the nucleic acid encoding it, for example resistance to proteolytic degradation; e) dimerization sequences, to allow for peptide dimerization; or f any combination of a), b), c), d), and e), as well as linker sequences as needed.

In a preferred embodiment, the fusion partner is a presentation structure. By "presentation structure" or grammatical equivalents herein is meant a sequence, which, when fused to candidate bioactive agents, causes the candidate agents to assume a conformationally restricted form. Proteins interact with each other largely through conformationally constrained domains. Although small peptides with freely rotating amino and carboxyl termini can have potent functions as is known in the art, the conversion of such peptide structures into pharmacologic agents is difficult due to the inability to predict side-chain positions for peptidomimetic synthesis. Therefore the presentation of peptides in conformationally constrained structures will benefit both the later generation of pharmaceuticals and will also likely lead to higher affinity interactions of the peptide with the target protein. This fact has been recognized in the combinatorial library generation systems using biologically generated short peptides in bacterial phage systems. A number of workers have constructed small domain molecules in which one might present randomized peptide structures.

While the candidate bioactive agents may be either nucleic acid or peptides, presentation structures are preferably used with peptide candidate agents. Thus, synthetic presentation structures, i.e. artificial polypeptides, are capable of presenting a randomized peptide as a conformationally-restricted domain. Generally such presentation structures comprise a first portion joined to the N-terminal end of the randomized peptide, and a second portion joined to the C-terminal end of the peptide; that is, the peptide is inserted into the presentation structure, although variations may be made, as outlined below. To increase the functional isolation of the randomized expression product, the presentation structures are selected or designed to have minimal biologically activity when expressed in the target cell.

Preferred presentation structures maximize accessibility to the peptide by presenting it on an exterior loop. Accordingly, suitable presentation structures include, but are not limited to, minibody structures, loops on beta-sheet turns and coiled-coil stem structures in which residues not critical to structure are randomized, zinc-finger domains, cysteine-linked (disulfide) structures, transglutaminase linked structures, cyclic peptides, B-loop structures, helical barrels or bundles, leucine zipper motifs, etc.

In a preferred embodiment, the presentation structure is a coiled-coil structure, allowing the presentation of the randomized peptide on an exterior loop. See, for example, Myszka et al., Biochem. 33:2362–2373 (1994), hereby incorporated by reference). Using this system investigators have isolated peptides capable of high affinity interaction with the appropriate target. In general, coiled-coil structures allow for between 6 to 20 randomized positions.

A preferred coiled-coil presentation structure is as follows: MGC<u>AALESEVSALESEVASLESEVAAL</u>GRGDMP <u>LAAVKSKLSAVKSKLASVKSKLM</u>CGPP SEQ ID NO: 7. The underlined regions represent a coiled-coil leucine zipper region defined previously (see Martin et al., EMBO J. 13(22):5303–5309 (1994), incorporated by reference). The bolded GRGDMP SEQ ID NO: 8 region represents the loop structure and when appropriately replaced with randomized peptides (i.e. candidate bioactive agents, generally depicted herein as $(X)_n$, SEQ ID NO: 9 where X is an amino acid residue and n is an integer of at least 5 or 6) can be of variable length. The replacement of the bolded region is facilitated by encoding restriction endonuclease sites in the underlined regions, which allows the direct incorporation of randomized oligonucleotides at these positions. For example, a preferred embodiment generates a XhoI site at the double underlined LE site and a HindIII site at the double-underlined KL site.

In a preferred embodiment, the presentation structure is a minibody structure. A "minibody" is essentially composed of a minimal antibody complementarity region. The minibody presentation structure generally provides two randomizing regions that in the folded protein are presented along a single face of the tertiary structure. See for example Bianchi et al., J. Mol. Biol. 236(2):649–59 (1994), and references cited therein, all of which are incorporated by reference). Investigators have shown this minimal domain is stable in solution and have used phage selection systems in combinatorial libraries to select minibodies with peptide regions exhibiting high affinity, $Kd=10^{-7}$, for the pro-inflammatory cytokine IL-6.

A preferred minibody presentation structure is as follows: MGRNSQATS<u>GFTFSHFY</u>MEWVRGGEYIAASR <u>HKHNKYT</u>TEYSASVKGRYIVSRDTSQSILYLQKKKGPP SEQ ID NO: 10. The bold, underline regions are the regions which may be randomized. The italized phenylalanine must be invariant in the first randomizing region. The entire peptide is cloned in a three-oligonucleotide variation of the coiled-coil embodiment, thus allowing two different randomizing regions to be incorporated simultaneously. This embodiment utilizes non-palindromic BstXI sites on the termini.

In a preferred embodiment, the presentation structure is a sequence that contains generally two cysteine residues, such that a disulfide bond may be formed, resulting in a conformationally constrained sequence. This embodiment is particularly preferred when secretory targeting sequences are used. As will be appreciated by those in the art, any number of random sequences, with or without spacer or linking sequences, may be flanked with cysteine residues. In other embodiments, effective presentation structures may be generated by the random regions themselves. For example, the random regions may be "doped" with cysteine residues which, under the appropriate redox conditions, may result in highly crosslinked structured conformations, similar to a presentation structure. Similarly, the randomization regions may be controlled to contain a certain number of residues to confer β-sheet or α-helical structures.

In a preferred embodiment, the fusion partner is a targeting sequence. As will be appreciated by those in the art, the localization of proteins within a cell is a simple method for increasing effective concentration and determining function. For example, RAF1 when localized to the mitochondrial membrane can inhibit the anti-apoptotic effect of BCL-2. Similarly, membrane bound Sos induces Ras mediated signaling in T-lymphocytes. These mechanisms are thought to rely on the principle of limiting the search space for ligands, that is to say, the localization of a protein to the plasma membrane limits the search for its ligand to that limited dimensional space near the membrane as opposed to the three dimensional space of the cytoplasm. Alternatively, the concentration of a protein can also be simply increased by nature of the localization. Shuttling the proteins into the nucleus confines them to a smaller space thereby increasing concentration. Finally, the ligand or target may simply be localized to a specific compartment, and inhibitors must be localized appropriately.

Thus, suitable targeting sequences include, but are not limited to, binding sequences capable of causing binding of the expression product to a predetermined molecule or class of molecules while retaining bioactivity of the expression product, (for example by using enzyme inhibitor or substrate sequences to target a class of relevant enzymes); sequences signalling selective degradation, of itself or co-bound proteins; and signal sequences capable of constitutively localizing the candidate expression products to a predetermined cellular locale, including a) subcellular locations such as the Golgi, endoplasmic reticulum, nucleus, nucleoli, nuclear membrane, mitochondria, chloroplast, secretory vesicles, lysosome, and cellular membrane; and b) extracellular locations via a secretory signal. Particularly preferred is localization to either subcellular locations or to the outside of the cell via secretion.

In a preferred embodiment, the targeting sequence is a nuclear localization signal (NLS). NLSs are generally short, positively charged (basic) domains that serve to direct the entire protein in which they occur to the cell's nucleus. Numerous NLS amino acid sequences have been reported including single basic NLS's such as that of the SV40 (monkey virus) large T Antigen (Pro Lys Lys Lys Arg Lys Val) SEQ ID NO: 11, Kalderon (1984), et al., Cell, 39:499–509; the human retinoic acid receptor-β nuclear localization signal (ARRRP) SEQ ID NO: 12; NFkB p50 EEVQRKRQKL SEQ ID NO: 13; Ghosh et al., Cell 62:1019 (1990); NFkB p65 (EEKRKRTYE SEQ ID NO: 14, Nolan et al., Cell 64:961 (1991); and others (see for example Boulikas, J. Cell. Biochem. 55(1):32–58 (1994), hereby incorporated by reference) and double basic NLS's exemplified by that of the Xenopus (African clawed toad) protein, nucleoplasmin,(Ala Val Lys Arg Pro Ala Ala Thr Lys Lys Ala Gly Gln Ala Lys Lys Lys Lys Leu Asp SEQ ID NO: 15), Dingwall, et al., Cell, 30:449–458, 1982 and Dingwall, et al., J. Cell Biol., 107:641–849; 1988). Numerous localization studies have demonstrated that NLSs incorporated in synthetic peptides or grafted onto reporter proteins not normally targeted to the cell nucleus cause these peptides and reporter proteins to be concentrated in the nucleus. See, for example, Dingwall, and Laskey, Ann, Rev. Cell Biol., 2:367–390, 1986; Bonnerot, et al., Proc. Natl. Acad. Sci. USA, 84:6795–6799, 1987; Galileo, et al., Proc. Natl. Acad. Sci. USA, 87:458–462, 1990.

In a preferred embodiment, the targeting sequence is a membrane anchoring signal sequence. This is particularly useful since many parasites and pathogens bind to the membrane, in addition to the fact that many intracellular events originate at the plasma membrane. Thus, membrane-bound peptide libraries are useful for both the identification of important elements in these processes as well as for the discovery of effective inhibitors. The invention provides methods for presenting the randomized expression product extracellularly or in the cytoplasmic space. For extracellular presentation, a membrane anchoring region is provided at the carboxyl terminus of the peptide presentation structure. The randomized epression product region is expressed on the cell surface and presented to the extracellular space, such that it can bind to other surface molecules (affecting their function) or molecules present in the extracellular medium. The binding of such molecules could confer function on the cells expressing a peptide that binds the molecule. The cytoplasmic region could be neutral or could contain a domain that, when the extracellular randomized expression product region is bound, confers a function on the cells (activation of a kinase, phosphatase, binding of other cellular components to effect function). Similarly, the randomized expression product-containing region could be contained within a cytoplasmic region, and the transmembrane region and extracellular region remain constant or have a defined function.

Membrane-anchoring sequences are well known in the art and are based on the genetic geometry of mammalian transmembrane molecules. Peptides are inserted into the membrane based on a signal sequence (designated herein as ssTM) and require a hydrophobic transmembrane domain (herein TM). The transmembrane proteins are inserted into the membrane such that the regions encoded 5' of the transmembrane domain are extracellular and the sequences 3' become intracellular. Of course, if these transmembrane domains are placed 5' of the variable region, they will serve to anchor it as an intracellular domain, which may be desirable in some embodiments. ssTMs and TMs are known for a wide variety of membrane bound proteins, and these sequences may be used accordingly, either as pairs from a particular protein or with each component being taken from a different protein, or alternatively, the sequences may be synthetic, and derived entirely from consensus as artificial delivery domains.

As will be appreciated by those in the art, membrane-anchoring sequences, including both ssTM and TM, are known for a wide variety of proteins and any of these may be used. Particularly preferred membrane-anchoring sequences include, but are not limited to, those derived from CD8, ICAM-2, IL-8R, CD4 and LFA-1.

Useful sequences include sequences from: 1) class I integral membrane proteins such as IL-2 receptor beta-chain (residues 1–26 are the signal sequence, 241–265 are the transmembrane residues; see Hatakeyama et al., Science 244:551 (1989) and von Heijne et al, Eur. J. Biochem. 174:671 (1988)) and insulin receptor beta chain (residues 1–27 are the signal, 957–959 are the transmembrane domain and 960–1382 are the cytoplasmic domain; see Hatakeyama, supra, and Ebina et al., Cell 40:747 (1985)); 2) class II integral membrane proteins such as neutral endopeptidase (residues 29–51 are the transmembrane domain, 2–28 are the cytoplasmic domain; see Malfroy et al., Biochem. Biophys. Res. Commun. 144:59 (1987)); 3) type III proteins such as human cytochrome P450 NF25 (Hatakeyama, supra); and 4) type IV proteins such as human P-glycoprotein (Hatakeyama, supra). Particularly preferred are CD8 and ICAM-2. For example, the signal sequences from CD8 and ICAM-2 lie at the extreme 5' end of the transcript. These consist of amino acids 1–32 in the case of CD8 (MASPLTRFLSLNLLLLGESILGSGEAKPQAP SEQ ID NO: 16, Nakauchi et al., PNAS USA 82:5126 (1985) and 1–21 in the case of ICAM-2 (MSSFG YRTLTVALFTLICCPG SEQ ID NO: 17; Staunton et al., Nature (London) 339:61 (1989)). These leader sequences deliver the construct to the membrane while the hydrophobic transmembrane domains, placed 3' of the random candidate region, serve to anchor the construct in the membrane. These transmembrane domains are encompassed by amino acids 145–195 from CD8 (PQRPE DCRPRGSVKGTGLD-FACDIYIWAPLAGICVALLLSLIIT LICYHSR SEQ ID NO: 18; Nakauchi, supra) and 224–256 from ICAM-2 (MVIIVTVVSVLLSLFVTSVLLCFIFGQH LRQQR SEQ ID NO: 19; Staunton, supra).

Alternatively, membrane anchoring sequences include the GPI anchor, which results in a covalent bond between the molecule and the lipid bilayer via a glycosyl-phosphatidylinositol bond for example in DAF (PNKGSGTTSGTTRLLSGHTCFTLTGLLGTLVTMGLLT SEQ ID NO: 20, with the bolded serine the site of the anchor; see Homans et al., Nature 333(6170):269–72 (1988), and Moran et al., J. Biol. Chem. 266:1250 (1991)). In order to do this, the GPI sequence from Thy-1 can be cassetted 3' of the variable region in place of a transmembrane sequence.

Similarly, myristylation sequences can serve as membrane anchoring sequences. It is known that the myristylation of c-src recruits it to the plasma membrane. This is a simple and effective method of membrane localization, given that the first 14 amino acids of the protein are solely responsible for this function: MGSSKSKPKDPSQR SEQ ID NO: 21 (see Cross et al., Mol. Cell. Biol. 4(9):1834 (1984); Spencer et al., Science 262:1019–1024 (1993), both of which are hereby incorporated by reference). This motif has already been shown to be effective in the localization of reporter genes and can be used to anchor the zeta chain of the TCR. This motif is placed 5' of the variable region in order to localize the construct to the plasma membrane. Other modifications such as palmitoylation can be used to anchor constructs in the plasma membrane; for example, palmitoylation sequences from the G protein-coupled receptor kinase GRK6 sequence (LLQRLFSRQ DCCGNCSD-SEEELPTRL SEQ ID NO: 22, with the bold cysteines being palmitolyated; Stoffel et al., J. Biol. Chem 269:27791, (1994)); from rhodopsin (KQFRNCMLTSLCCGKNPLGD SEQ ID NO: 23; Barnstable et al., J. Mol. Neurosci. 5(3) :207 (1994)); and the p21 H-ras 1 protein (LNPPDESGPGCMSCKCVLS SEQ ID NO: 24; Capon et al., Nature 302:33 (1983)).

In a preferred embodiment, the targeting sequence is a lysozomal targeting sequence, including, for example, a lysosomal degradation sequence such as Lamp-2 (KFERQ SEQ ID NO: 25; Dice, Ann. N.Y. Acad. Sci. 674:58 (1992); or lysosomal membrane sequences from Lamp-1 (MLIPIAGFFALAGLVLIVLIAYL*IGRKRSHAGYQTI* SEQ ID NO: 26, Uthayakumar et al., Cell. Mol. Biol. Res. 41:405 (1995)) or Lamp-2 (LVPIAVGMLAGVLILV LLAY-FIGL*KHHHAGYEQF* SEQ ID NO: 27, Konecki et al., Biochem. Biophys. Res. Comm. 205:1–5 (1994), both of which show the transmembrane domains in italics and the cytoplasmic targeting signal underlined).

Alternatively, the targeting sequence may be a mitrochondrial localization sequence, including mitochondrial matrix sequences (e.g. yeast alcohol dehydrogenase Ill; MLRTSS- LFTRRVQPSLFSRNlLRLQST SEQ ID NO: 28; Schatz, Eur. J. Biochem. 165:1–6 (1987)); mitochondrial inner membrane sequences (yeast cytochrome c oxidase subunit IV; MLSLRQSIRFFKPATRTLCSSRYLL SEQ ID NO: 29; Schatz, supra); mitochondrial intermembrane space sequences (yeast cytochrome c1; MFSMLSKRWAQRTL-SKSFYSTATGMSKSGKLTQKLVTAGVAAAGITASTL LYADSLTAEAMTA SEQ ID NO: 30; Schatz, supra) or mitochondrial outer membrane sequences (yeast 70 kD outer membrane protein MKSFITRNKTAILATVAATG-TAIGAYYYNQLQQQQQRGKK SEQ ID NO: 31; Schatz supra).

The target sequences may also be endoplasmic reticulum sequences, including the sequences from calreticulin (KDEL SEQ ID NO: 32; Pelham, Royal Society London Transactions B; 1–10 (1992)) or adenovirus E3/19K protein (LYLSRRSFIDEKKMP SEQ ID NO: 33; Jackson et al., EMBO J. 9:3153 (1990).

Furthermore, targeting sequences also include peroxisome sequences (for example, the peroxisome matrix sequence from Luciferase; SKL; Keller et al., PNAS USA 4:3264, (1987)); farnesylation sequences (for example, P21 H-ras 1; LNPPDESGPGCMSCKCVLS SEQ ID NO: 34; with the bold cysteine farnesylated; Capon, supra); geranylgeranylation sequences (for example, protein rab-5A; LTEPTQPTRNQCCSN SEQ ID NO: 35; with the bold cyteines geranylgeranylated; Farnsworth, PNAS USA 91:11963 (1994)); or destruction sequences (cyclin B1; RTALGDIGN SEQ ID NO: 36; Klotzbucher et al., EMBO J. 1:3053 (1996)).

In a preferred embodiment, the targeting sequence is a secretory signal sequence capable of effecting the secretion of the candidate translation product. There are a large number of known secretory signal sequences which are placed 5' to the variable peptide region, and are cleaved from the peptide region to effect secretion into the extracellular space. Secretory signal sequences and their transferability to unrelated proteins are well known, e.g., Silhavy, et al. (1985) Microbiol. Rev. 49, 398–418. This is particularly useful to generate a peptide capable of binding to the surface of, or affecting the physiology of, a target cell that is other than the host cell, e.g., the cell expressing the peptide. In a preferred approach, a fusion product is configured to contain, in series, secretion signal peptide-presentation structure-randomized expression product region-presentation structure. In this manner, target cells grown in the vicinity of cells caused to express the library of peptides, are bathed in secreted peptide. Target cells exhibiting a physiological change in response to the presence of a peptide, e.g., by the peptide binding to a surface receptor or by being internalized and binding to intracellular targets, and the secreting cells are localized by any of a variety of selection schemes and the peptide causing the effect determined. Exemplary effects include variously that of a designer cytokine (i.e., a stem cell factor capable of causing hematopoietic stem cells to divide and maintain their totipotential), a factor causing cancer cells to undergo spontaneous apoptosis, a factor that binds to the cell surface of target cells and labels them specifically, etc.

Suitable secretory sequences are known, including signals from IL-2 (MYRMQLLSCIALSLALVTNS SEQ ID NO: 37; Villinger et al., J. Immunol. 155:3946 (1995)), growth hormone, (MATGSRTSLLLAFGLLCLPWLQEGSA<u>FPT</u> SEQ ID NO: 38; Roskam et al., Nucleic Acids Res. 7:30 (1979)); preproinsulin (MALWMRLLPLLALLALWGPD PAA<u>FVN</u> SEQ ID NO: 39; Bell et al., Nature 284:26 (1980)); and influenza HA protein (MKAKLLVLLYAFVAG <u>DQI</u> SEQ ID NO: 40; Sekiwawa et al., PNAS 80:3563)), with cleavage between the non-underlined-underlined junction. A particularly preferred secretory signal sequence is the signal leader sequence from the secreted cytokine IL-4, which comprises the first 24 amino acids of IL-4 as follows: MGLTSQLLPPLFFLLACAGNFVHG SEQ ID NO: 41.

In a preferred embodiment, the fusion partner is a rescue sequence. A rescue sequence is a sequence which may be used to purify or isolate either the candidate agent or the nucleic acid encoding it. Thus, for example, peptide rescue sequences include purification sequences such as the His$_6$ tag for use with Ni affinity columns and epitope tags for detection, immunoprecipitation or FACS (fluorescence-activated cell sorting). Suitable epitope tags include myc (for use with the commercially available 9E1 0 antibody), the BSP biotinylation target sequence of the bacterial enzyme BirA, flu tags, lacZ, and GST.

Alternatively, the rescue sequence may be a unique oligonucleotide sequence which serves as a probe target site to allow the quick and easy isolation of the retroviral construct, via PCR, related techniques, or hybridization.

In a preferred embodiment, the fusion partner is a stability sequence to confer stability to the candidate bioactive agent or the nucleic acid encoding it. Thus, for example, peptides may be stabilized by the incorporation of glycines after the initiation methionine (MG or MGG0), for protection of the peptide to ubiquitination as per Varshavsky's N-End Rule, thus conferring long half-life in the cytoplasm. Similarly, two prolines at the C-terminus impart peptides that are largely resistant to carboxypeptidase action. The presence of two glycines prior to the prolines impart both flexibility and prevent structure initiating events in the di-proline to be propagated into the candidate peptide structure. Thus, preferred stability sequences are as follows: MG(X)$_n$GGPP SEQ ID NO: 42, where X is any amino acid and n is an integer of at least four.

In one embodiment, the fusion partner is a dimerization sequence. A dimerization sequence allows the non-covalent association of one random peptide to another random peptide, with sufficient affinity to remain associated under normal physiological conditions. This effectively allows small libraries of random peptides (for example, $10^4$) to become large libraries if two peptides per cell are generated which then dimerize, to form an effective library of $10^8$ ($10^4 \times 10^4$). It also allows the formation of longer random peptides, if needed, or more structurally complex random peptide molecules. The dimers may be homo- or heterodimers.

Dimerization sequences may be a single sequence that self-aggregates, or two sequences, each of which is generated in a different retroviral construct. That is, nucleic acids encoding both a first random peptide with dimerization sequence 1, and a second random peptide with dimerization sequence 2, such that upon introduction into a cell and expression of the nucleic acid, dimerization sequence 1 associates with dimerization sequence 2 to form a new random peptide structure.

Suitable dimerization sequences will encompass a wide variety of sequences. Any number of protein-protein interaction sites are known. In addition, dimerization sequences may also be elucidated using standard methods such as the yeast two hybrid system, traditional biochemical affinity binding studies, or even using the present methods. See also U.S. patent application Ser. No. 09/285,912, hereby expressly incorporated by reference in its entirety.

In addition, the peptides may be made as a part of a fusion protein; see PCT US99/23715, hereby expressly incorporated by reference.

The fusion partners may be placed anywhere (i.e. N-terminal, C-terminal, internal) in the structure as the biology and activity permits.

In a preferred embodiment, the fusion partner includes a linker or tethering sequence, as generally described in PCT US 97/01019, that can allow the candidate agents to interact with potential targets unhindered. For example, when the candidate bioactive agent is a peptide, useful linkers include glycine-serine polymers (including, for example, $(GS)_n$, $(GSGGS)_n$ SEQ ID NO: 43, and $(GSGGS)_n$ SEQ ID NO: 44, where n is an integer of at least one), glycine-alanine polymers, alanine-serine polymers, and other flexible linkers such as the tether for the shaker potassium channel, and a large variety of other flexible linkers, as will be appreciated by those in the art. Glycine-serine polymers are preferred since both of these amino acids are relatively unstructured, and therefore may be able to serve as a neutral tether between components. Secondly, serine is hydrophilic and therefore able to solubilize what could be a globular glycine chain. Third, similar chains have been shown to be effective in joining subunits of recombinant proteins such as single chain antibodies.

In addition, the fusion partners, including presentation structures, may be modified, randomized, and/or matured to alter the presentation orientation of the randomized expression product. For example, determinants at the base of the loop may be modified to slightly modify the internal loop peptide tertiary structure, which maintaining the randomized amino acid sequence.

In a preferred embodiment, combinations of fusion partners are used. Thus, for example, any number of combinations of presentation structures, targeting sequences, rescue sequences, and stability sequences may be used, with or without linker sequences.

Thus, candidate agents can include these components, and may then be used to generate a library of fragments, each containing a different random nucleotide sequence that may encode a different peptide. The ligation products are then transformed into bacteria, such as *E. coli*, and DNA is prepared from the resulting library, as is generally outlined in Kitamura, PNAS USA 92:9146–9150 (1995), hereby expressly incorporated by reference.

Delivery of the library DNA into a retroviral packaging system results in conversion to infectious virus. Suitable retroviral packaging system cell lines include, but are not limited to, the Bing and BOSC23 cell lines described in WO 94/19478; Soneoka et al., Nucleic Acid Res. 23(4):628 (1995); Finer et al., Blood 83:43 (1994); Pheonix packaging lines such as PhiNX-eco and PhiNX-ampho, described below; 292T+gag-pol and retrovirus envelope; PA317; and cell lines outlined in Markowitz et al., Virology 167:400 (1988), Markowitz et al., J. Virol. 62:1120 (1988), Li et al., PNAS USA 93:11658 (1996), Kinsella et al., Human Gene Therapy 7:1405 (1996), all of which are incorporated by reference. Preferred systems include PhiNX-eco and PhiNX-ampho or similar cell lines, disclosed in PCT US97/01019.

When the cells are not replicating, other viral vectors may be used, including adenoviral vectors, feline immunoviral (FIV) vectors, etc.

In a preferred embodiment, when the candidate agent is introduced to the cells using a viral vector, the candidate peptide agent is linked to a detectable molecule, and the methods of the invention include at least one expression assay. An expression assay is an assay that allows the determination of whether a candidate bioactive agent has been expressed, i.e. whether a candidate peptide agent is present in the cell. Thus, by linking the expression of a candidate agent to the expression of a detectable molecule such as a label, the presence or absence of the candidate peptide agent may be determined. Accordingly, in this embodiment, the candidate agent is operably linked to a detectable molecule. Generally, this is done by creating a fusion nucleic acid. The fusion nucleic acid comprises a first nucleic acid encoding the candidate bioactive agent (which can include fusion partners, as outlined above), and a second nucleic acid encoding a detectable molecule. The terms "first" and "second" are not meant to confer an orientation of the sequences with respect to 5'-3' orientation of the fusion nucleic acid. For example, assuming a 5'-3' orientation of the fusion sequence, the first nucleic acid may be located either 5' to the second nucleic acid, or 3' to the second nucleic acid. Preferred detectable molecules in this embodiment include, but are not limited to, fluorescent proteins, including GFP, YFP, BFP and RFP, with the former being especially preferred.

The candidate nucleic acids are introduced into the cells to screen for bioactive agents capable of eliminating multi-drug resistance. By "introduced into" or grammatical equivalents herein is meant that the nucleic acids enter the cells in a manner suitable for subsequent expression of the nucleic acid. The method of introduction is largely dictated by the targeted cell type, discussed below. Exemplary methods include $CaPO_4$ precipitation, liposome fusion, lipofectin®, electroporation, viral infection, etc. The candidate nucleic acids may stably integrate into the genome of the host cell (for example, with retroviral introduction, outlined below), or may exist either transiently or stably in the cytoplasm (i.e. through the use of traditional plasmids, utilizing standard regulatory sequences, selection markers, etc.). As many pharmaceutically important screens require human or model mammalian cell targets, retroviral vectors capable of transfecting such targets are preferred.

In a preferred embodiment, the candidate nucleic acids are part of a retroviral particle which infects the cells. Generally, infection of the cells is straightforward with the application of the infection-enhancing reagent polybrene, which is a polycation that facilitates viral binding to the target cell. Infection can be optimized such that each cell generally expresses a single construct, using the ratio of virus particles to number of cells. Infection follows a Poisson distribution.

Alternatively, when candidate agents other than nucleic acids or the peptides encoded by them are used, the candidate agents are added to the cells in any number of ways, as will be appreciated by those in the art.

The candidate agents are added to cells. As will be appreciated by those in the art, the type of cells used in the present invention can vary widely. Basically, any mammalian cells may be used, with mouse, rat, primate and human cells being particularly preferred, although as will be appreciated by those in the art, modifications of the system by pseudotyping allows all eukaryotic cells to be used, preferably higher eukaryotes.

Accordingly, suitable cell types include, but are not limited to, tumor cells of all types (particularly melanoma, myeloid leukemia, carcinomas of the lung, breast, ovaries, colon, kidney, prostate, pancreas and testes), cardiomyocytes, endothelial cells, epithelial cells, lymphocytes (T-cell and B cell), mast cells, eosinophils, vascular intimal cells, hepatocytes, leukocytes including mononuclear leukocytes, stem cells such as haemopoetic, neural, skin, lung, kidney, liver and myocyte stem cells (for use in screening for differentiation and de-differentiation factors), osteoclasts, chondrocytes and other connective tissue cells, keratinocytes, melanocytes, liver cells, kidney cells, and adipocytes. Suitable cells also include known research cells, including, but not limited to, Jurkat T cells, NIH3T3 cells, CHO, Cos, H1299, MDMB435S, A549, HeLa, etc. See the ATCC cell line catalog, hereby expressly incorporated by reference.

In one embodiment, the cells may be genetically engineered, that is, contain exogeneous nucleic acid, for example, to contain target molecules.

In a preferred embodiment, a plurality of cells is screened. That is, the cells into which the candidate nucleic acids are introduced are screened as outlined herein. By a "plurality of cells" herein is meant roughly from about $10^3$ cells to $10^8$ or $10^9$, with from $10^6$ to $10^8$ being preferred. This plurality of cells comprises a cellular library, wherein generally each cell within the library contains a member of the retroviral molecular library, i.e. a different candidate nucleic acid, although as will be appreciated by those in the art, some cells within the library may not contain a retrovirus, and some may contain more than one. Alternatively, when non-retroviral candidate agents are used, each cell is the same, and different cells get exposed to different candidate agents. When methods other than retroviral infection are used to introduce the candidate nucleic acids into a plurality of cells, the distribution of candidate nucleic acids within the individual cell members of the cellular library may vary widely, as it is generally difficult to control the number of nucleic acids which enter a cell during electroporation, etc.

In a preferred embodiment, the candidate nucleic acids are introduced into a plurality of cells, and the protective effect of the candidate bioactive agents is reexamined in naive HeLa cells as described below.

If necessary, the cells are treated to conditions suitable for the expression of the candidate nucleic acids (for example, when inducible promoters are used), to produce the candidate expression products, either translation or transcription products.

As outlined herein, there are two basic types of screens that can be done. In a preferred embodiment, libraries of candidate agents are used to screen for compounds that result in a multidrug phenotype; that is, for example, peptides that confer the MDR phenotype are used to identify target molecules within the MDR pathway. Once these have been identified, as is outlined herein with the identification of XAPC7 and Zeta, which, when inhibited by the RGP8.5 peptide (also identified herein) confer multidrug resistance, the XAPC7 and/or Zeta molecules can be used in screens for candidate drugs that bind to them and modulate their activity.

In general, the candidate agents are added to the cells (either extracellulany or intracellularly, as outlined above) under reaction conditions that favor agent-target interactions. Generally, this will be physiological conditions. Incubations may be performed at any temperature which facilitates optimal activity, typically between 4 and 40° C. Incubation periods are selected for optimum activity, but may also be optimized to facilitate rapid high through put screening. Typically between 0.1 and 1 hour will be sufficient. Excess reagent is generally removed or washed away.

A variety of other reagents may be included in the assays. These include reagents like salts, neutral proteins, e.g. albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for detection. Washing or rinsing the cells will be done as will be appreciated by those in the art at different times, and may include the use of filtration and centrifugation. When second labeling moieties (also referred to herein as "secondary labels") are used, they are preferably added after excess non-bound target molecules are removed, in order to reduce non-specific binding; however, under some circumstances, all the components may be added simultaneously.

Thus, in a preferred embodiment, the present invention provides for screens of candidate agents that can confer or ameliorate multidrug resistance. By "multi-drug resistance" or other grammatical equivalents herein is meant the simultaneous loss of sensitivity to multiple chemotherapeutic drugs. Cells which acquire MDR may be detected by phenotypic changes. Suitable phenotypic changes include, but are not limited to: gross physical changes such as changes in cell morphology, cell growth, cell viability, adhesion to substrates or other cells, and cellular density; changes in the expression of one or more RNAs, proteins, lipids, hormones, cytokines, or other molecules; changes in the equilibrium state (i.e. half-life) or one or more RNAs, proteins, lipids, hormones, cytokines, or other molecules; changes in the localization of one or more RNAs, proteins, lipids, hormones, cytokines, or other molecules; changes in the bioactivity or specific activity of one or more RNAs, proteins, lipids, hormones, cytokines, receptors, or other molecules; changes in the secretion of ions, cytokines, hormones, growth factors, or other molecules; alterations in cellular membrane potentials, polarization, integrity or transport; changes in infectivity, susceptibility, latency, adhesion, and uptake of viruses and bacterial pathogens; etc.

By "capable of conferring an MDR phenotype" herein is meant the bioactive agent changes the sensitivity of the cell, such that the cell survives treatment with a chemotherapeutic agent.

The MDR phenotype may be detected in a wide variety of ways, as is described more fully below. Generally, the MDR phenotype is detected using, for example: microscopic analysis of cell morphology; standard cell viability assays, standard labeling assays such as fluorometric indicator assays for the presence or level of a particular cell or molecule, including FACS or other dye staining techniques; biochemical detection of the expression of target compounds after killing the cells; etc.

In a preferred embodiment, the MDR phenotype is detected in the cell in which the randomized nucleic acid was introduced. The MDR phenotype is detected by treating cells with a lethal dose of a chemotherapeutic drug and isolating the surviving clones. By "lethal dose" herein is meant a concentration of a chemotherapeutic drug sufficient to kill 99.99% of the cells.

By "treated" herein is meant that the cells are incubated with a chemotherapeutic drug for a time sufficient to detect a MDR phenotype. The concentration of the chemotherapeutic drug will vary depending on the identity of the drug, but can range from 1 nm to 100 $\mu$M. Chemotherapeutic drugs useful in the methods of the present invention include taxol, etoposide, cisplatin, adriamycin, mitoxantrone, camptothecin, vincristine, etc. See also any of the anti-neoplastic agents outlined in the 11$^{th}$ Edition of the Merck Index, including alkylating agents and antibiotics, hereby incorporated by reference.

In a preferred embodiment, Taxol is used. In general, the concentration of Taxol used ranges from 1 nm to 100 pM. In a preferred embodiment, cells are treated with 100–200 nM, Taxol for 48 to 72 hours. In a particularly preferred embodiment, cells are treated with 200 nM Taxol for forty eight hours.

An "MDR phenotype" of a cell indicates the presence of a bioactive agent.

In a preferred embodiment, once a cell with an MDR phenotype is detected, the cell is isolated from the plurality which do not have MDR phenotypes. This may be done in any number of ways, as is known in the art, and will in some instances depend on the assay or screen. Suitable isolation techniques include, but are not limited to, FACS, lysis selection using complement, cell cloning, scanning by Fluorimager, expression of a "survival" protein, induced expression of a cell surface protein or other molecule that can be rendered fluorescent or taggable for physical isolation; expression of an enzyme that changes a non-fluorescent molecule to a flourescent one; overgrowth against a background of no or slow growth; death of cells and isolation of DNA or other cell vitality indicator dyes, etc.

In a preferred embodiment, surviving clones are isolated and retreated with the same concentration of the chemotherapeutic drug to eliminate clones whose outgrowth is due to non-heritable, stochastic, or transitory resistance.

In a preferred embodiment, the candidate nucleic acid and/or the bioactive agent is isolated from the positive cell. This may be done in a number of ways. In a preferred embodiment, primers complementary to DNA regions common to the retroviral constructs, or to specific components of the library such as a rescue sequence, defined above, are used to "rescue" the unique random sequence. Alternatively, the bioactive agent is isolated using a rescue sequence. Thus, for example, rescue sequences comprising epitope tags or purification sequences may be used to pull out the bioactive agent, using immunoprecipitation or affinity columns. In some instances, as is outlined below, this may also pull out the primary target molecule, if there is a sufficiently strong binding interaction between the bioactive agent and the target molecule. Alternatively, the peptide may be detected using mass spectroscopy.

Once rescued, the sequence of the bioactive agent and/or bioactive nucleic acid is determined. This information can then be used in a number of ways.

In a preferred embodiment, the bioactive agent is resynthesized and reintroduced into the target cells, to verify the effect. This may be done using retroviruses, or alternatively using fusions to the HIV-1 Tat protein, and analogs and related proteins, which allows very high uptake into target cells. See for example, Fawell et al., PNAS USA 91:664 (1994); Frankel et al., Cell 55:1189 (1988); Savion et al., J. Biol. Chem. 256:1149 (1981); Derossi et al., J. Biol. Chem. 269:10444 (1994); and Baldin et al., EMBO J. 9:1511 (1990), all of which are incorporated by reference.

In a preferred embodiment, a clonogenic survival assay in naive HeLa cells is used. Resynthesizing and reintroducing bioactive agents which confer multi-drug resistance allows screening for constructs which enable growth at higher concentrations of the chemotherapeutic drug used in the initial selection process. These agents can be selected for further study as outlined below.

Thus, the methods of the present invention comprise identifying and isolating bioactive agents capable of conferring or ameliorating MDR. Bioactive agents capable of conferring MDR are defined herein as "resistance conferring" (RC) agents, defined above. Bioactive agents capable of ameliorating MDR are defined herein as "sensitizing" agents, defined below.

In one embodiment, a RC agent is a peptide that interacts with or modulates a PRP protein to confer a MDR phenotype in the presence of a chemotherapeutic agent(s). In a preferred embodiment, the RC peptide comprises the amino acid sequence set forth in FIG. 7A SEQ ID NO: 1.

In alternative embodiments, the bioactive agent is a RC peptide having at least 90% sequence identity to the sequence set forth in FIG. 7A SEQ ID NO: 1.

In some embodiments, the RC peptide is encoded and preferably expressed by an RC nucleic acid (see for example, FIG. 7B SEQ ID NO: 2).

In a preferred embodiment, the sequence of a bioactive agent is used to generate more candidate bioactive agents. For example, the sequence of the bioactive agent may be the basis of a second round of (biased) randomization, to develop bioactive agents with increased or altered activities. Alternatively, the second round of randomization may change the affinity of the bioactive agent. Furthermore, it may be desirable to put the identified random region of the bioactive agent into other presentation structures, or to alter the sequence of the constant region of the presentation structure, to alter the conformation/shape of the bioactive agent. It may also be desirable to "walk" around a potential binding site, in a manner similar to the mutagenesis of a binding pocket, by keeping one end of the ligand region constant and randomizing the other end to shift the binding of the peptide around.

In a preferred embodiment, either the bioactive agent or the bioactive nucleic acid encoding it is used to identify target molecules, i.e. the molecules with which the bioactive agent interacts. As will be appreciated by those in the art, there may be primary target molecules, to which the bioactive agent binds or acts upon directly, and there may be secondary target molecules, which are part of the signalling pathway affected by the bioactive agent; these might be termed "validated targets".

In a preferred embodiment, the bioactive agent is used to pull out target molecules, such as the XAPC7 and Zeta molecules herein. For example, as outlined herein, if the target molecules are proteins, the use of epitope tags or purification sequences can allow the purification of primary target molecules via biochemical means (co-immunoprecipitation, affinity columns, etc.). Alternatively, the peptide, when expressed in bacteria and purified, can be used as a probe against a bacterial cDNA expression library made from mRNA of the target cell type. Or, peptides can be used as "bait" in either yeast or mammalian two or three hybrid systems. Such interaction cloning approaches have been very useful to isolate DNA-binding proteins and other interacting protein components. The peptide(s) can be combined with other pharmacologic activators to study the epistatic relationships of signal transduction pathways in question. It is also possible to synthetically prepare labeled peptide bioactive agent and use it to screen a cDNA library expressed in bacteriophage for those cDNAs which bind the peptide. Furthermore, it is also possible that one could use cDNA cloning via retroviral libraries to "complement" the effect induced by the peptide. In such a strategy, the peptide would be required to be stochiometrically titrating away some important factor for a specific signaling pathway. If this molecule or activity is replenished by over-expression of a cDNA from within a cDNA library, then one can clone the target. Similarly, cDNAs cloned by any of the above yeast or bacteriophage systems can be reintroduced to mammalian cells in this manner to confirm that they act to complement function in the system the peptide acts upon.

Once primary target molecules have been identified, secondary target molecules may be identified in the same manner, using the primary target as the "bait". In this manner, signaling pathways may be elucidated. Similarly, bioactive agents specific for secondary target molecules may also be discovered, to allow a number of bioactive agents to act on a single pathway, for example for combination therapies.

In a preferred embodiment, PRP proteins identified in the first screen, such as XPCA7, are used in secondary screens of candidate agents to identify drug compounds that will modulate the activity of the PRP proteins, for use in methods of treating MDR. In this embodiment, the PRP target molecules are used in binding and bioactivity screens. By "target molecules" herein is meant PRP proteins and nucleic acids which render cells resistant to chemotherapeutic drugs. In a preferred embodiment, PRP proteins are proteasome alpha type subunit XPCA7 and proteasome alpha type subunit Zeta.

An PRP protein of the present invention may be identified in several ways. "Protein" in this sense includes proteins, polypeptides, and peptides. An PRP nucleic acid or protein is initially identified by, substantial nucleic acid and/or amino acid sequence homology to the sequences shown in FIG. 8 SEQ ID NOS: 3–6. Such homology can be based upon the overall nucleic acid or amino acid sequence.

As used herein, a protein is a "PRP protein" if the overall homology of the protein sequence to the amino acid sequences shown in FIGS. 8B SEQ ID NO: 4 and 8D SEQ ID NO: 6 is preferably greater than about 50%, more preferably greater than about 60%, even more preferably greater than about 75% and most preferably greater than 80. In some embodiments the homology will be as high as about 90 to 95 or 98%.

Homology in this context means sequence similarity or identity, with identity being preferred. This homology will be determined using standard techniques known in the art, such as the Best Fit sequence program described by Devereux et al., *Nucl. Acid Res.* 12:387–395 (1984), preferably using the default settings, or the BLASTX program (Altschul et al., *J. Mol. Biol.* 215, 403–410). The alignment may include the introduction of gaps in the sequences to be aligned. In addition, for sequences which contain either more or fewer amino acids than the proteins shown in FIGS. 8B SEQ ID NO: 4 and 8D SEQ ID NO: 6, it is understood that the percentage of homology will be determined based on the number of homologous amino acids in relation to the total number of amino acids. Thus, for example, homology of sequences shorter than that shown in FIGS. 8B SEQ ID NO: 4 and 8D SEQ ID NO: 6, as discussed below, will be determined using the number of amino acids in the shorter sequence.

Similarity is determined using standard techniques known in the art, including, but not limited to, the algorithm of Smith & Waterman, Adv. Appl. Math. 2:482 (1981), by the algorithm of Needleman & Wunsch. J. Mol. Biol. 1970. 48:443, by the search for similarity method of Pearson & Lipman. 1988. PNAS USA 85:2444, by computerized implementations of these algorithms (GAP, BESTFIT, FASTA, and TFASTA in the Wisconsin Genetics Software Package, Genetics Computer Group, 575 Science Drive, Madison, Wis.), or the Best Fit sequence program described by Devereux et al Nucl. Acid Res. 1984. 12:387–395.

In a preferred embodiment, percent identity or similarity is calculated by FastDB based upon the following parameters: mismatch penalty of 1.0; gap penalty of 1.0; gap size penalty of 0.33, joining penalty of 30.0. ("Current Methods in Comparison and Analysis", Macromolecule Sequencing and Synthesis, Selected Methods and Applications, pp. 127–149, 1998. Alan R. Liss, Inc.).

Another example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng and Doolittle. J. Mol. Evol. 1987. 35:351–360; the method is similar to that described by Higgins and Sharp. 1989. CABIOS 5:151–153. Useful PILEUP parameters including a default gap weight of 3.00, a default gap length weight of 0.10, and weighted end gaps.

An additional example of a useful algorithm is the BLAST algorithm, described in Altschul et al. J. Mol. Biol. 1990. 215:403410 and Karlin et al., PNAS USA 1993. 90:5873–5787. A particularly useful BLAST program is the WU-BLAST-2 program which was obtained from Altschul et al., Methods in Enzymology. 1996. 266: 460480; [http://blast.wustl/edu/blast/README.html]. WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity.

In an alternative embodiment, percent amino acid sequence identity is determined. In percent identity calculations relative weight is not assigned to various manifestations of sequence variation, such as, insertions, deletions, substitutions, etc. Only identities are scored positively (+1) and all forms of sequence variation given a value of "0", which obviates the need for a weighted scale or parameters as described above for sequence similarity calculations. Therefore, percent identity represents a highly rigorous method of comparing sequences.

Percent sequence identity can be calculated, for example, by dividing the number of matching identical residues by the total number of residues of the "shorter" sequence in the aligned region and multiplying by 100. The "longer" sequence is the one having the most actual residues in the aligned region.

PRP proteins of the present invention may be shorter or longer than the amino acid sequences shown in FIGS. 8B SEQ ID NO: 4 and 8D SEQ ID NO: 6. Thus in a preferred embodiment, included within the definition of MDR proteins are portions or fragments of the sequences depicted in FIGS. 8B SEQ ID NO: 4 and 8D SEQ ID NO: 6. For example, MDR deletion mutants can be made.

In a preferred embodiment, the PRP proteins are derivative or variant PRP proteins. That is, as outlined more fully below, the derivative PRP peptides will contain at least one amino acid substitution, deletion or insertion, with amino acid substitutions being particularly preferred. The amino acid substitution, insertion or deletion may occur at any residue within the PRP peptide.

In addition, as is more fully outlined below, PRP proteins can be made that are longer than those depicted in FIGS. 8B SEQ ID NO: 4 and 8D SEQ ID NO: 6, for example, by the addition of epitope or purification tags, the addition of other fusion sequences, etc.

PRP proteins may also be identified as being encoded by PRP nucleic acids. Thus, PRP proteins are encoded by nucleic acids that will hybridize to the sequences depicted in FIGS. 8A SEQ ID NO: 3 and 8C SEQ ID NO: 5 or its complement, as outlined herein.

In a preferred embodiment, when the PRP proteins are to be used to generate antibodies, the PRP proteins must share at least one epitope or determinant with their respective full length proteins shown in FIGS. 8B SEQ ID NO: 4 and 8D SEQ ID NO: 6. By "epitope" or "determinant" herein is meant a portion of a protein which will generate and/or bind an antibody. Thus, in most instances, antibodies made to a smaller PRP protein will be able to bind to the full length protein. In a preferred embodiment, the epitope is unique; that is, antibodies generated to a unique epitope show little or no cross-reactivity.

In a preferred embodiment, the antibodies to PRP proteins are capable of reducing or eliminating the biological function of PRP proteins, as is described below. For example, the addition of anti-PRP antibodies (either polyclonal or preferably monoclonal) to PRP (or cells containing PRP) also may reduce or eliminate the PRP activity. Generally, at least a 25% decrease in activity is preferred, with at least about 50% being particularly preferred and about a 95–100% decrease being especially preferred.

Antibodies of the invention specifically bind to PRP proteins. By "specifically bind" herein is meant that the antibodies bind to the protein with a binding constant in the range of at least $10^{-4}$–$10^{-6}$ M$^{-1}$, with a preferred range being $10^{-7}$–$10^{-9}$ M$^{-1}$.

In the case of the nucleic acid, the overall homology of the nucleic acid sequence is commensurate with amino acid homology but takes into account the degeneracy in the genetic code and codon bias of different organisms. Accordingly, the nucleic acid sequence homology may be either lower or higher than that of the protein sequence. Thus the homology of the nucleic acid sequence as compared to the nucleic acid sequence of either FIG. 8A SEQ ID NO: 3 or FIG. 8C SEQ ID NO: 5 is preferably greater than 75%, more preferably greater than about 80%, particularly greater than about 85% and most preferably greater than 90%. In some embodiments the homology will be as high as about 93 to 95 or 98%.

Nucleic acid similarity can be determined using, for example, BLASTN (Altschul et al. 1990. J. Mol. Biol. 147:195–197). BLASTN uses a simple scoring system in which matches count +5 and mismatches –4. To achieve computational efficiency, the default parameters have been incorporated directly into the source code.

In a preferred embodiment, PRP nucleic acids encode, an PRP protein, such as proteasome alpha type subunits XAPC7 or Zeta. As will be appreciated by those in the art, due to the degeneracy of the genetic code, an extremely large number of nucleic acids may be made, all of which encode the PRP proteins of the present invention. Thus, having identified a particular amino acid sequence, those skilled in the art could make any number of different nucleic acids, by simply modifying the sequence of one or more codons in a way which does not change the amino acid sequence of the encoded PRP protein.

In one embodiment, the nucleic acid homology is determined through hybridization studies. Thus, for example, nucleic acids which hybridize under high stringency to the nucleic acid sequences shown in FIG. 8A SEQ ID NO: 3 and/or 8C SEQ ID NO: 5 or their complements are considered an PRP gene.

High stringency conditions are known in the art; see for example Maniatis et al., Molecular Cloning: A Laboratory Manual, 2d Edition, 1989, and Short Protocols in Molecular Biology, ed. Ausubel, et al., both of which are hereby incorporated by reference.

High stringency conditions are known in the art; see for example Maniatis et al., Molecular Cloning: A Laboratory Manual, 2d Edition, 1989, and Short Protocols in Molecular Biology, ed. Ausubel, et al., Hames and Higgins, eds. *Nucleic Acid Hybridization, A Practical Approach*, IL press, Washington, D.C., 1985; Berger and Kimmel eds. *Methods in Enzymology, Vol. 52, Guide to Molecular Cloning Techniques*, Academic press Inc., New York, N.Y., 1987; and Bothwell, Yancopoulos and Alt, eds, *Methods for Cloning and Analysis of Eukaryotic Gene*, Jones and Bartlett Publishers, Boston, Mass. 1990, which are hereby expressly incorporated by reference in their entirety.

The choice of hybridization conditions will be evident to one skilled in the art and will generally be guided by the purpose of the hybridization, the type of hybridization (DNA-DNA, DNA-RNA, RNA-RNA, oligonucleotide-DNA etc.), and the level of desired relatedness between the sequences. Methods for hybridization are well established in the literature. For example, one or ordinary skill in the art realizes that the stability of nucleic acid duplexes will decrease with an increased number and proximity of mismatched bases; thus, the stringency of hybridization may be used to maximize or minimize the stability of such duplexes. Hybridiziation stringency can be altered by, for example, adjusting the temperature of hybridization solution; adjusting the percentage of helix-destabilizing agents, such as, formamide, in the hybridization solution; and adjusting the temperature and salt concentration of the wash solutions. In general, the stringency of hybridization is adjusted during the post-hybridization washes by varying the salt concentration and/or the temperature. Stringency of hybridization may be increased, for example, by: i) increasing the percentage of formamide in the hybridization solution; ii) increasing the temperature of the wash solution; or iii) decreasing the ionic strength of the wash solution. High stringency conditions may involve high temperature hybridization (e.g. 65° C.–68° C. in aqueous solution containing 4–6×SSC, or 42° C. in 50% formamide) combined with high temperature (e.g., 5° C.–25° C. below the $T_m$) and a low salt concentration (e.g., 0.1×SSC) washes. Reduced stringency conditions may involve lower hybridization temperatures (e.g., 35° C.–42° C. in 20–50% formamide) with intermediate temperature (e.g., 40° C.–60° C.) washes in a higher salt concentration (e.g., 2–6×SSC). Moderate stringency conditions, which may involve hybridization at a temperature between 50° C.–55° C. and washes in 0.1×SSC, 0.1% SDS at between 50° C. and 55° C., may be used (see Maniatis and Ausubel, supra). In a preferred embodiment, nucleic acids which hybridize to the nucleic acids herein have the biological activity as described herein.

The PRP proteins and nucleic acids of the present invention are preferably recombinant. As used herein, "nucleic acid" may refer to either DNA or RNA, or molecules which contain both deoxy- and ribonucleotides. The nucleic acids include genomic DNA, cDNA and oligonucleotides including sense and anti-sense nucleic acids. Such nucleic acids may also contain modifications in the ribose-phosphate backbone to increase stability and half life of such molecules in physiological environments.

The nucleic acid may be double stranded, single stranded, or contain portions of both double stranded or single stranded sequence. As will be appreciated by those in the art, the depiction of a single strand ("Watson") also defines the sequence of the other strand ("Crick"); thus the sequence depicted in FIGS. 7B SEQ ID NO: 2 and 8A SEQ ID NO: 3 and 8C SEQ ID NO: 5 also complement of the sequences. By the term "recombinant nucleic acid" herein is meant nucleic acid, originally formed in vitro, in general, by the manipulation of nucleic acid by endonucleases, in a form not normally found in nature. Thus an isolated PRP nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

Similarly, a "recombinant protein" is a protein made using recombinant techniques, i.e. through the expression of a recombinant nucleic acid as depicted above. A recombinant protein is distinguished from naturally occurring protein by at least one or more characteristics. For example, the protein may be isolated or purified away from some or all of the proteins and compounds with which it is normally associated in its wild type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of an MDR protein from one organism in a different organism or host cell. Alternatively, the protein may be made at a significantly higher concentration than is normally seen, through the use of a inducible promoter or high expression promoter, such that the protein is made at increased concentration levels. Alternatively, the protein may be in a form not normally found in nature, as in the addition of an epitope tag or amino acid substitutions, insertions and deletions, as discussed below.

Also included within the definition of PRP proteins of the present invention are amino acid sequence variants. These variants fall into one or more of three classes: substitutional, insertional or deletional variants. These variants ordinarily are prepared by site specific mutagenesis of nucleotides in the DNA encoding PRP proteins XAPC7 and Zeta, using cassette or PCR mutagenesis or other techniques well known in the art, to produce DNA encoding the variant, and thereafter expressing the DNA in recombinant cell culture as outlined above. However, variant PRP protein fragments having up to about 100–150 residues may be prepared by in vitro synthesis using established techniques. Amino acid sequence variants are characterized by the predetermined nature of the variation, a feature that sets them apart from naturally occurring allelic or interspecies variation of the PRP protein amino acid sequences. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed PRP variants screened for the optimal combination of desired activity. Techniques for making substitution mutations at predetermined sites in DNA having a known sequence are well known, for example, M13 primer mutagenesis and PCR mutagenesis. Screening of the mutants is done using survival assays of PRP protein activities; for example, resistance to Taxol.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of PRP protein are desired, substitutions are generally made in accordance with the following chart:

CHART I

| Original Residue | Exemplary Substitutions |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Chart I. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g. leucyl, isoleucyl, phenylalanyl, valyl or, alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

In an alternative embodiment, a library of variants are generated by an entirely, non-specific, random mutagenesis method. These techniques are known in the art and do not require the selection of a specific cite or region to be altered. For example, DNA shuffling as described by Stemmer, *Nature* 370:389–391 (1994) and Stemmer. *PNAS USA* 91:10747–10751 (1994)) can be used to produce variants which are cloned, expressed, and screened for a desired property. For example, the intracellular activity of an PRP protein can be increased or decreased.

The variants typically exhibit the same qualitative biological activity and will elicit the same immune response as the naturally-occurring analogue, although variants also are selected to modify the characteristics of the PRP protein as needed. Alternatively, the variant may be designed such that the biological activity of the PRP protein is altered. For example, glycosylation sites may be altered or removed.

Covalent modifications of PRP polypeptides are included within the scope of this invention. One type of covalent modification includes reacting targeted amino acid residues of an PRP polypeptide with an organic derivatizing agent that is capable of reacting with selected side chains or the N- or C-terminal residues of an PRP polypeptide. Derivatization with bifunctional agents is useful, for instance, for crosslinking an PRP protein to a water-insoluble support matrix or surface for use in the method for purifying anti-PRP antibodies, respectively, or screening assays, as is more fully described below. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidyl-propionate), bifunctional maleimides such as bis-N-maleimido-1,8-octane and agents such as methyl-3-((p-azidophenyl)dithiolpropioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the amino groups of lysine, arginine, and histidine side chains [T. E. Creighton, *Proteins: Structure and Molecular Properties*, W.H. Freeman & Co., San Francisco, pp. 79–86 (1983)], acetylation of the N-terminal amine, and amidation of any C-terminal carboxyl group.

Another type of covalent modification of the PRP proteins included within the scope of this invention comprises altering the native glycosylation pattern of the polypeptide. "Altering the native glycosylation pattern" is intended for purposes herein to mean deleting one or more carbohydrate moieties found in a native sequence of a PRP polypeptide, and/or adding one or more glycosylation sites that are not present in the native sequences of an PRP polypeptide.

Addition of glycosylation sites to PRP polypeptides may be accomplished by altering the amino acid sequence thereof. The alteration may be made, for example, by the addition of, or substitution by, one or more serine or threonine residues to the native sequences of PRP polypeptides (for O-linked glycosylation sites). The PRP amino acid sequence may optionally be altered through changes at the DNA level, particularly by mutating the DNA encoding an PRP polypeptide at preselected bases such that codons are generated that will translate into the desired amino acids.

Another means of increasing the number of carbohydrate moieties on the PRP proteins is by chemical or enzymatic coupling of glycosides to the polypeptide. Such methods are described in the art, e.g., in WO 87/05330 published Sep. 11, 1987, and in Aplin and Wriston, *CRC Crit. Rev. Biochem.*, pp. 259–306 (1981).

Removal of carbohydrate moieties present on PRP polypeptides may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo- and exo-glycosidases as described by Thotakura et al., *Meth. Enzymol.*, 138:350 (1987).

Another type of covalent modification of PRP proteins comprise linking the polypeptides to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

The PRP proteins of the present invention may also be modified in a way to form chimeric molecules comprising an PRP polypeptide fused to another, heterologous polypeptide or amino acid sequence. In one embodiment, such a chimeric molecule comprises a fusion of an PRP polypeptide with a tag polypeptide which provides an epitope to which an anti-tag antibody can selectively bind. The epitope tag is generally placed at the amino-or carboxyl-terminus of an PRP polypeptide. The presence of such epitope-tagged forms of an PRP polypeptide can be detected using an antibody against the tag polypeptide. Also, provision of the epitope tag enables the PRP polypeptide to be readily purified by affinity purification using an anti-tag antibody or another type of affinity matrix that binds to the epitope tag. In an alternative embodiment, the chimeric molecule may comprise a fusion of an PRP polypeptide with an immunoglobulin or a particular region of an immunoglobulin. For a bivalent form of the chimeric molecule, such a fusion could be to the Fc region of an IgG molecule.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.*, 8:2159–2165 (1988)]; the c-myc tag and the 8F9, 3C7, 6E10, G4, B7 and 9E10 antibodies thereto [Evan et al., *Molecular and Cellular Biology*, 5:3610–3616 (1985)]; and the Herpes Simplex virus glycoprotein D (gD) tag and its antibody [Paborsky et al., *Protein Engineering*, 3(6):547–553 (1990)]. Other tag polypeptides include the Flag-peptide [Hopp et al., *BioTechnology*, 6:1204–1210 (1988)]; the KT3 epitope peptide [Martin et al., *Science*, 255:192–194 (1992)]; tubulin epitope peptide [Skinner et al., *J. Biol. Chem.*, 266:15163–15166 (1991)]; and the T7 gene 10 protein peptide tag [Lutz-Freyermuth et al., *Proc. Natl. Acad. Sci. USA*, 87:6393–6397 (1990)].

Once an PRP nucleic acid is identified, it can be cloned and, if necessary, its constituent parts recombined to form the entire PRP nucleic acid. Once isolated from its natural source, e.g., contained within a plasmid or other vector or excised therefrom as a linear nucleic acid segment, the recombinant PRP nucleic acid can be further-used as a probe to identify and isolate other PRP nucleic acids. It can also be used as a "precursor" nucleic acid to make modified or variant PRP nucleic acids and proteins.

Using the nucleic acids of the present invention which encode an PRP protein, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the PRP protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. The transcriptional and translational regulatory nucleic acid will generally be appropriate to the host cell used to express the PRP protein; for example, transcriptional and translational regulatory nucleic acid sequences from Bacillus are preferably used to express the PRP protein in Bacillus. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention.

In addition, the expression vector may comprise additional elements. For example, the expression vector may have two replication systems, thus allowing it to be maintained in two organisms, for example in mammalian or insect cells for expression and in a procaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

A preferred expression vector system is a retroviral vector system such as is generally described in PCT/US97/01019 and PCT/US97/01048, both of which are hereby expressly incorporated by reference.

The PRP proteins of the present invention are produced by culturing a host cell transformed with an expression vector containing nucleic acid encoding an PRP protein, under the appropriate conditions to induce or cause expression of the encoded protein. The conditions appropriate for PRP protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archebacteria, fungi, and insect and animal cells, including mammalian cells. Of particular interest are *Drosophila melangaster* cells, *Saccharomyces cerevisiae* and other yeasts, *E. coli, Bacilus subtilis*, SF9 cells, C129 cells, 293 cells, Neurospora, BHK, CHO, COS, and HeLa cells, fibroblasts, Schwanoma cell lines, immortalized mammalian myeloid and lymphoid cell lines, Jurkat cells, mast cells and other endocrine and exocrine cells, and neuronal cells.

In a preferred embodiment, the PRP proteins are expressed in mammalian cells. Mammalian expression systems are also known in the art, and include retroviral systems. A mammalian promoter is any DNA sequence capable of binding mammalian RNA polymerase and initiating the downstream (3') transcription of a coding sequence for the PRP protein into mRNA. A promoter will have a transcription initiating region, which is usually placed proximal to the 5' end of the coding sequence, and a TATA box, using a located 25–30 base pairs upstream of the transcription initiation site. The TATA box is thought to direct RNA polymerase 11 to begin RNA synthesis at the correct site. A mammalian promoter will also contain an upstream promoter element (enhancer element), typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenlytion signals include those derived form SV40.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei.

In a preferred embodiment, PRP proteins are expressed in bacterial systems. Bacterial expression systems are well known in the art.

A suitable bacterial promoter is any nucleic acid sequence capable of binding bacterial RNA polymerase and initiating the downstream (3') transcription of the coding sequence of PRP protein into mRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription.

In addition to a functioning promoter sequence, an efficient ribosome binding site is desirable. In *E. coli*, the ribosome binding site is called the Shine-Delgamo (SD) sequence and includes an initiation codon and a sequence 3–9 nucleotides in length located 3–11 nucleotides upstream of the initiation codon.

The expression vector may also include a signal peptide sequence that provides for secretion of the PRP protein in bacteria. The signal sequence typically encodes a signal peptide comprised of hydrophobic amino acids which direct the secretion of the protein from the cell, as is well known in the art. The protein is either secreted into the growth media (gram-positive bacteria) or into the periplasmic space, located between the inner and outer membrane of the cell (gram-negative bacteria).

The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways.

These components are assembled into expression vectors. Expression vectors for bacteria are well known in the art, and include vectors for *Bacillus subtilis, E. coli, Streptococcus cremoris*, and *Streptococcus lividans*, among others.

The bacterial expression vectors are transformed into bacterial host cells using techniques well known in the art, such as calcium chloride treatment, electroporation, and others.

In one embodiment, PRP protein is produced in insect cells. Expression vectors for the transformation of insect cells, and in particular, baculovirus-based expression vectors, are well known in the art.

In a preferred embodiment, PRP protein is produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe*, and *Yarrowia lipolytica*. Preferred promoter sequences for expression in yeast include the inducible GAL1, 10 promoter, the promoters from alcohol dehydrogenase, enolase, glucokinase, glucose-6-phosphate isomerase, glyceraldehyde-3-phosphate-dehydrogenase, hexokinase, phosphofructokinase, 3-phosphoglycerate mutase, pyruvate kinase, and the acid phosphatase gene. Yeast selectable markers include ADE2, HIS4, LEU2, TRP1, and ALG7, which confers resistance to tunicamycin; the neomycin phosphotransferase gene, which confers resistance to G418; and the CUP1 gene, which allows yeast to grow in the presence of copper ions.

The PRP protein may also be made as a fusion protein, using techniques well known in the art. Thus, for example, for the creation of monoclonal antibodies, if the desired epitope is small, the PRP protein may be fused to a carrier protein to form an immunogen. Alternatively, the PRP protein may be made as a fusion protein to increase expression, or for other reasons. For example, when the PRP protein is a peptide, the nucleic acid encoding the peptide may be linked to other nucleic acid for expression purposes.

In one embodiment, the PRP nucleic acids, proteins and antibodies of the invention are labeled. By "labeled" herein is meant that a compound has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the compound at any position.

In a preferred embodiment, the PRP protein is purified or isolated after expression. PRP proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the PRP protein may be purified using a standard affinity column using antibody specific for the PRP protein. Ultrafiltration and diafiltration techniques, in conjunction with protein concentration, are also useful. For general guidance in suitable purification techniques, see Scopes, R., Protein Purification, Springer-Verlag, NY (1982). The degree of purification necessary will vary depending on the use of the PRP protein. In some instances no purification will be necessary.

Once expressed and purified if necessary, the PRP proteins and nucleic acids are useful in a number of applications.

In a preferred embodiment, the PRP proteins, nucleic acids, modified proteins and cells containing the native or modified PRP proteins are used in screening assays. Identification of important PRP proteins permits the design of drug screening assays for compounds that modulate PRP activity. Thus, in this embodiment, the methods comprise combining an PRP protein sample and a candidate bioactive agent, and evaluating the effect on multi-drug resistance. By "PRP activity" or grammatical equivalents herein is meant either the decrease or loss of MDR. In a preferred embodiment, PRP activity is the loss of MDR.

In a preferred embodiment, the activity of the PRP protein is increased; in another preferred embodiment, the activity of the PRP protein is decreased. Thus, bioactive agents that are antagonists are preferred in some embodiments, and bioactive agents that are agonists may be preferred in other embodiments.

Screens may be designed to first find candidate agents that can bind to PRP proteins, and then these agents may be used in assays that evaluate the ability of the candidate agent to modulate PRP activity. Thus, as will be appreciated by those in the art, there are a number of different assays which may be run, i.e., binding assays and activity assays.

Thus, in one embodiment, the methods comprise combining an PRP protein and a candidate bioactive agent, and determining the binding of the candidate agent to the PRP protein. Preferred embodiments utilize the human PRP protein, although other eucaryotic proteins may also be used, including rodents (mice, rats, hamsters, guinea pigs, etc.), farm animals (cows, sheep, pigs, horses, etc.) primates and yeast. These latter embodiments may be preferred in the development of animal models of human disease. In some embodiments, as outlined herein, variant or derivative PRP proteins may be used, including deletion PRP proteins as outlined above.

Furthermore, included within the definition of PRP proteins are portions of PRP proteins; that is, either the full-length protein may be used, or functional portions thereof. In addition, the assays described herein may utilize either isolated PRP proteins or cells comprising the PRP proteins.

Generally, in a preferred embodiment of the methods herein, the PRP protein or the candidate agent is non-diffusably bound to an insoluble support having isolated sample receiving areas (e.g. a microtiter plate, an array, etc.). The insoluble supports may be made of any composition to which the compositions can be bound, is readily separated from soluble material, and is otherwise compatible with the overall method of screening. The surface of such supports may be solid or porous and of any convenient shape. Examples of suitable insoluble supports include microtiter plates, arrays, membranes and beads. These are typically made of glass, plastic (e.g., polystyrene), polysaccharides, nylon or nitrocellulose, teflon™, etc. Microtiter plates and arrays are especially convenient because a large number of assays can be carried out simultaneously, using small amounts of reagents and samples. The particular manner of binding of the composition is not crucial so long as it is compatible with the reagents and overall methods of the invention, maintains the activity of the composition and is nondiffusable. Preferred methods of binding include the use of antibodies (which do not sterically block either the ligand binding site or activation sequence when the protein is bound to the support), direct binding to "sticky" or ionic supports, chemical crosslinking, the synthesis of the protein or agent on the surface, etc. Following binding of the protein or agent, excess unbound material is removed by washing. The sample receiving areas may then be blocked through incubation with bovine serum albumin (BSA), casein or other innocuous protein or other moiety.

In a preferred embodiment, the PRP protein is bound to the support, and a candidate bioactive agent is added to the assay. Alternatively, the candidate agent is bound to the support and the PRP protein is added. Novel binding agents include specific antibodies, non-natural binding agents identified in screens of chemical libraries, peptide analogs, etc. Of particular interest are screening assays for agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The determination of the binding of the candidate bioactive agent to the PRP protein may be done in a number of ways. In a preferred embodiment, the candidate bioactive agent is labeled, and binding determined directly. For example, this may be done by attaching all or a portion of the PRP protein to a solid support, adding a labeled candidate agent (for example a fluorescent label), washing off excess reagent, and determining whether the label is present on the solid support. Various blocking and washing steps may be utilized as is known in the art.

By "labeled" herein is meant that the compound is either directly or indirectly labeled with a label which provides a detectable signal, e.g. radioisotope, fluorescers, enzyme, antibodies, particles such as magnetic particles, chemiluminescers, or specific binding molecules, etc. Specific binding molecules include pairs, such as biotin and streptavidin, digoxin and antidigoxin, etc. For the specific binding members, the complementary member would normally be labeled with a molecule which provides for detection, in accordance with known procedures, as outlined above. The label can directly or indirectly provide a detectable signal.

In some embodiments, only one of the components is labeled. For example, the proteins (or proteinaceous candidate agents) may be labeled at tyrosine positions using $^{125}I$, or with fluorophores. Alternatively, more than one component may be labeled with different labels; using $^{125}I$ for the proteins, for example, and a fluorophor for the candidate agents.

In a preferred embodiment, the binding of the candidate bioactive agent is determined through the use of competitive binding assays. In this embodiment, the competitor is a binding moiety known to bind to the target molecule (i.e. an PRP protein), such as an antibody, peptide, binding partner, ligand, etc. In a preferred embodiment, the competitor is the peptide of FIG. 7A SEQ ID NO: 1. Under certain cirumstances, there may be competitive binding as between the bioactive agent and the binding moiety, with the binding moiety displacing the bioactive agent.

In one embodiment, the candidate bioactive agent is labeled. Either the candidate bioactive agent, or the competitor, or both, is added first to the protein for a time sufficient to allow binding, if present. Incubations may be performed at any temperature which facilitates optimal activity, typically between 4 and 40° C. Incubation periods are selected for optimum activity, but may also be optimized to facilitate rapid high through put screening. Typically between 0.1 and 1 hour will be sufficient. Excess reagent is generally removed or washed away. The second component is then added, and the presence or absence of the labeled component is followed, to indicate binding.

Screening for agents that modulate the activity of PRP proteins may also be done. In preferred embodiments, methods for screening for a bioactive agent capable of modulating the activity of a PRP protein comprise the steps of adding a candidate bioactive agent to a sample of a PRP proteins, as described above, and determining an alteration in the biological activity of the PRP protein. "Modulating the activity of a PRP protein" includes an increase in activity, a decrease in activity, or a change in the type or kind of activity present. Thus, the candidate agent should bind to the PRP protein (although this may not be necessary), and alter its biological or biochemical activity as defined herein. The methods include both in vivo screening methods, as are generally outlined above, and in vivo screening of cells for alterations in the phenotype of a PRP protein, including but not limited to, changes in the presence, distribution, activity or amount of the PRP protein.

In a preferred embodiment, the competitor is added first, followed by the candidate bioactive agent. Displacement of the competitor is an indication that the candidate bioactive agent is binding to the PRP protein and thus is capable of binding to, and potentially modulating, the activity of the PRP protein. In this embodiment, either component can be labeled. Thus, for example, if the competitor is labeled, the presence of label in the wash solution indicates displacement by the agent. Alternatively, if the candidate bioactive agent is labeled, the presence of the label on the support indicates displacement.

In a preferred embodiment, modulation by the candidate bioactive agent is determined through the use of competitive assays. In this embodiment, the candidate bioactive agent is added first, with incubation and washing, followed by the competitor. The absence of modulation of the PRP protein by the competitor may indicate that the bioactive agent is bound to the PRP protein with a higher affinity. Thus, if the candidate bioactive agent is labeled, the presence of the label on the support, coupled with a lack of competitor binding, may indicate that the candidate agent is capable of binding to the PRP protein In a preferred embodiment, the methods comprise differential screening to identity bioactive agents that are capable of modulating the activity of the PRP proteins. In this embodiment, the methods comprise combining an PRP protein and a competitor in a first sample. A second sample comprises a candidate bioactive agent, an PRP protein and a competitor. The binding of the competitor is determined for both samples, and a change, or difference in binding between the two samples indicates the presence of an agent capable of binding to the PRP protein and potentially modulating its activity. That is, if the binding of the competitor is different in the second sample relative to the first sample, the agent is capable of binding to the PRP protein.

Alternatively, another embodiment utilizes differential screening to identify drug candidates that bind to the native PRP protein, but cannot bind to modified PRP proteins. The structure of the PRP protein may be modeled, and used in rational drug design to synthesize agents that interact with that site. Drug candidates that affect PRP bioactivity are also identified by screening drugs for the ability to either enhance or reduce the activity of the protein.

Positive controls and negative controls may be used in the assays, as described herein. Preferably all control and test samples are performed in at least triplicate to obtain statistically significant results. Incubation of all samples is for a time sufficient for the binding of the agent to the protein. Following incubation, all samples are washed free of non-specifically bound material and the amount of bound, generally labeled agent determined. For example, where a radiolabel is employed, the samples may be counted in a scintillation counter to determine the amount of bound compound.

A variety of other reagents may be included in the screening assays. These include reagents like salts, neutral proteins, e.g. albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

In a preferred embodiment, the invention provides methods for screening for bioactive agents capable of modulating the phenotype of a PRP protein in a cell (Mirski, et al., (1987) *Cancer Res.*, 47, 2594–2598). By modulating the phenotype of a PRP protein herein is meant changes in, for example, the presence, distribution, activity or amount of the PRP protein. In a preferred embodiment, changes in the activity of the PRP protein is determined. The methods comprise adding a candidate bioactive agent, as defined above, to a cell comprising PRP proteins. Preferred cell types include almost any cell, as described herein. The cells either express PRP proteins from a endogenous gene or from a recombinant nucleic acid. In a preferred embodiment, a library of candidate agents are tested on a plurality of cells. Alternatively, a screen is preformed in the presence or absence of a competitive inhibitor and the PRP phenotype is determined.

Once identified, the PRP proteins and bioactive agents may find use as therapeutic agents in compositions used in the treatment of a multi-drug resistance associated disease. Bioactive agents which find use as therapeutic agents are referred to herein as "sensitzing agents". "Sensitizing agents" are any molecule that when added to a cell inhibits resistance to an chemotherapeutic agent(s). Sensitizing agents may be added separately or in combination with chemotherapeutic agents.

The present discovery relating to the role of PRP proteins in multi-drug resistance provides methods for ameliorating or eliminating MDR. In a preferred embodiment, the PRP proteins, particularly XPAC7 and Zeta and/or fragments thereof, are useful in the study or treatment of conditions which are mediated by MDR., i.e. to diagnose, treat, or prevent MDR associated diseases. Thus, "MDR" or "MDR associated diseases" or "disease state" include conditions whereby cells lose their sensitivity to chemotherapeutic agents mediated via any number of mechanisms, including upregulation of MDR-1.

The compositions and methods provided herein are particularly deemed useful for the treatment of multi-drug resistance associated with cancer, including solid tumors such as skin, breast, brain, cervical carcinomas, testicular carcinomas, etc. More particularly, cancers that may be treated by the compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinarv tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver; hepatoma (hepatocellular carcinoma), cholangiocarcinoma, hepatoblastom, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumdrs), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosathecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma [embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term a "cancerous cell" as provided herein, includes a cell afflicted by any one of the above identified conditions.

Thus, in one embodiment, methods of modulating MDR in cells or organisms are provided. In one embodiment, the methods comprise administering to a cell an anti-PRP antibody that reduces or eliminates the biological activity of the corresponding endogeneous PRP proteins. Alternatively, the methods comprise administering to a cell or organism a recombinant nucleic acid encoding an PRP protein. As will be appreciated by those in the art, this may be accomplished in any number of ways. In a preferred embodiment, the gene therapy techniques include the incorporation of the exogeneous gene using enhanced homologous recombination (EHR), for example as described in PCT/US93/03868, hereby incorporated by reference in its entirety.

In one embodiment, the invention provides methods for diagnosing an MDR related condition in an individual. The methods comprise measuring the activity of an PRP protein in a tissue from the individual or patient, which may include a measurement of the amount or specific activity of PRP proteins XAPC7 and Zeta. This activity is compared to the activity of XAPC7 and Zeta from either a unaffected second individual or from an unaffected tissue from the first individual. When these activities are different, the first individual may be at risk for an MDR mediated disorder.

In one embodiment, the PRP proteins of the present invention may be used to generate polyclonal and monoclonal antibodies to PRP proteins, which are useful as described herein. Similarly, the PRP proteins can be coupled, using standard technology, to affinity chromatography columns. These columns may then be used to purify PRP antibodies. In a preferred embodiment, the antibodies are generated to epitopes unique to an PRP protein; that is, the antibodies show little or no cross-reactivity to other proteins. These antibodies find use in a number of applications. For example, the PRP antibodies may be coupled to standard affinity chromatography columns and used to purify PRP proteins. The antibodies may also be used as blocking polypeptides, as outlined above, since they will specifically bind to PRP proteins.

In one embodiment, a therapeutically effective dose of a sensitizing agent is administered to a patient. By "therapeutically effective dose" herein is meant a dose that produces the effects for which it is administered. The exact dose will depend on the purpose of the treatment, and will be ascertainable by one skilled in the art using known techniques. As is known in the art, adjustments for degradation of the sensitizing agent, systemic versus localized delivery, and rate of new protease synthesis, as well as the age, body weight, general health, sex, diet, time of administration, drug interaction and the severity of the condition may be necessary, and will be ascertainable with routine experimentation by those skilled in the art.

A "patient" for the purposes of the present invention includes both humans and other animals and organisms, such as experimental animals. Thus the methods are applicable to both human therapy and veterinary applications. In a preferred embodiment, the patient is a human.

The administration of the compositions of the present invention can be done in a variety of ways, including, but not limited to, orally, subcutaneously, intravenously, intranasally, transdermally, intraperitoneally, intramuscularly, intrapulmonary, vaginally, rectally, or intraocularly. In some instances, for example, in the treatment of wounds and inflammation, the composition may be directly applied as a solution or spray. Depending upon the manner of introduction, the compounds may be formulated in a variety of ways. The concentration of therapeutically active compound in the formulation may vary from about 0.1–100 wt. %.

The pharmaceutical compositions of the present invention comprise a compound in a form suitable for administration to a patient. In the preferred embodiment, the pharmaceutical compositions are in a water soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The pharmaceutical compositions may also include one or more of the following: carrier proteins such as serum albumin; buffers; fillers such as microcrystalline cellulose, lactose, corn and other starches; binding agents; sweeteners and other flavoring agents; coloring agents; and polyethylene glycol. Additives are well known in the art, and are used in a variety of formulations.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All patents, patent applications, publications and references cited herein are expressly incorporated by reference.

EXAMPLES

Example 1

Isolation of Peptides that Confer Taxol Resistance in HeLa Cells

Experimental Protocols:

Cell culture and vector construction. Phoenix-ampho cells (293T with integrated viral packaging genes) (Pear, W. S. et al., (1993) Proc. Natl Acad. Sci. USA, 90, 9392–8396) and Hela tTA cells (Hela expressing tet activator) (Clontech) were used for retroviral transduction and Taxol sensitivity experiments, respectively. Information on Phoenix-ampho can be obtained at www.stanford.edu/group/nolan. The retroviral vector was used for peptide library construction as indicated in FIG. 1A. GFP-peptide fusions were cloned into the Tra vector as shown in FIG. 1A, replacing GFP with the fusion protein and with no peptide in the primary expression position.

Random peptide library construction A peptide library was constructed containing random 18 mers flanked with MGEFLIVIKS($X_{18}$)EFLIVIKSGPP SEQ ID NO: 45. The FLIVIKS SEQ ID NO: 46 sequence is derived from a study where the SKVILFE SEQ ID NO: 47 sequence was shown to form dimers in solution (Bodenmuller, H., et al., (1986) *EMBO J.*, 5, 1825–29). Our studies demonstrate the FLIVIKS SEQ ID NO: 46 sequence demonstrates a strong capacity to self-anneal and create protease-resistant scaffolded structures. Two oligos, RG221 (5'-GATCCCACCA CCATGGGCGAGTTCTTGATCGTGAAGTCAGGG (NNK)$_{18}$GGAGAATTCCTTATCGTC) and RG203 (GATCCCAATTTAATGGGAATCAGGTTTTAAGGAGG CCCTGATTTGACGATAAGGAATTCTCC-3')SEQ ID NO: 49, were annealed and extended. The double-strand product was purified and subsequently ligated into BstXI-digested retroviral vector as shown in FIG. 1A.

Peptide synthesis. The RG8.5 peptide synthesis was carried out on a fully automated Rainin Symphony/MultiplexTm peptide synthesizer (Tucson, Ariz.) following classical Fmoc-chemistry using Fmoc-Pro-Novasyn-TGT resin. Standard Fmoc-compatible side-chain-protection groups were used and the coupling reactions were carried out twice with a five-fold excess of Fmoc-protected alpha-amino acids adopting BOP/DIPEA mediated coupling method (Castro, B., et al., (1975) *Tetrahedron Lett.*, 14, 1219–1222). After assembling all the amino acids followed by the spacer (Acap, aminocaproic acid) and the biotin at the N-terminus, peptide was cleaved from the resin, purified by RP-HPLC and its integrity was confirmed by electrospray ionization-mass spectrometry (ESI-MS) as described earlier (Gururaja, T. L., and Levine, M. J., (1996) *Peptide Res.*, 3, 283–289).

Peptide library screening. The peptide library was transfected into Phoenix-ampho cells by calcium phosphate precipitation (Ausubel, F. M., et al., (1994). "Transfection of DNA into eukaryotic cells", In Curr. Prot. Mol. Biol. 1, 9.1.1–9.1.3). After 24 hours, the viral supernatant was used to infect $4 \times 10^8$ Hela cells for 48 hours. Cells were then plated in 15-cm dishes ($4 \times 10^6$ per dish). 24 hours later, cells were treated with 200 nM Taxol for 48 hours. Following Taxol treatment, the cells were washed with PBS once, re-fed with fresh medium every three days and then changed to conditioned medium containing 40% Hela growing medium. After two weeks, individual surviving clones were isolated and retreated with the same dosage of Taxol to eliminate clones whose outgrowth was due to non-heritable, stochastic, or transitory resistance.

RT-PCR for peptide rescue and MDR1 mRNA level assay. Peptide sequences were rescued by RT-PCR from Taxol-resistant cells and later cloned into a Tra vector (in which the peptide expression was under tetracycline control). Each peptide was re-tested in naive Hela cells by a clonogenic survival assay. For semi-quantitative PCR to measure MDR-1 mRNA level, RiboGreen RNA quantification kit (Molecular Probes) and 0.5 mg of total RNA were used for reverse transcription. Oligonucleotides for amplification of MDR-1 mRNA were described previously (Chen, G. et al., (1997) *J. Biol. Chem.*, 272, 5974–5982).

Clonogenic survival assay. Viruses carrying the rescued peptides were used to infect Hela cells as described above. After infection, $2 \times 10^5$ cells were seeded into single well of 6-well plate w/o Doxycycline (200 ng/ml) in the medium. 24 hours later, the cells were treated with Taxol for 48 hours. Two weeks after Taxol treatment, the Taxol-resistant clones were stained with Giemsa solution, photographed and enumerated.

Results:

The functional screening started with the creation of a large library of potentially expressed peptides in a retroviral delivery construct. Short peptides (see materials and methods) were encoded into the expression cassette by oligonucleotide synthesis. A peptide library consisting of more than $3 \times 108$ different peptides was constructed. The expression construct is shown in FIG. 1A. The peptide insert is expressed, after reverse transcription and interation of the delivered retrovirus, under the control of a retroviral promoter. An internal translation initiation site (IRES) was used for translation of the co-expressed GFP marker, which acts as a surrogate indicator of peptide expression levels and infection efficiency. The goal is to express sufficiently large numbers of different peptide motifs (aptmers) within cells and set genetic selection criteria for the cells that point to those rare peptides that have a dominant effect upon a pathway of interest. An overview of the genetic screen is outlined in FIG. 1A.

To make recombinant virus, the DNA library was transfected into the retroviral producer cell line Phoenix-Ampho. The infectious viral supernatant was harvested 48 hours later. Fresh supernatant was immediately used to infect $4 \times 10^8$ Hela cells. After a period of two days, during which retroviral integration finalizes and peptide expression reaches maximal levels, the cells were subjected to "Taxol selection pressure". More than 99.99% of the infected cells died after treatment with 200 nM Taxol .for 48 hours. After two weeks of growth in fresh media, 150 surviving clones were picked and retreated with the same dosage of Taxol to test for and eliminate clones whose original outgrowth had been due to false-positive breakthrough (i.e., rare cells that are resistant to Taxol by non-heritable mechanisms not related to peptide expression). The peptide sequences from the clones that remained Taxol resistant were rescued by RT-PCR and re-cloned into a Tetracycline-regulated retroviral vector (Tra) as shown in FIG. 1B. Each Taxol resistant clone rescued on average two different peptide sequences. This suggests a highly efficient infection had occurred and that the complete library was likely to have been represented during the infection and selection. We expected that only a single peptide from each surviving was actually capable of potentially eliciting the anti-apoptotic effect.

The protective effect of these peptides was re-examined by a clonogenic assay in naive HeLa cells. Peptide expression in the absence of doxycycline (Dox) was inferred by the expression of the GFP reporter (see construct in FIG. 1A). 150 clones were tested. Several peptides gave rise to constructs that, when re-introduced into target cells, gave rise to a significantly greater number of survivors when challenged with Taxol in the absence of Dox (peptide expression is on) than in the presence of Dox (peptide expression is off) (FIG. 1B). As a control, cells that expressed only GFP did not produce more surviving clones in the presence of Dox as compared to the absence of Dox (data not shown). This survival was shown to be Taxol-concentration dependent, with fewer survivors growing at higher concentrations of the drug. The insert of one retroviral clone, named RGP8.5, was chosen for further study due to the strength of its effect. RGP8.5 contained a 40 amino acid peptide, (MGEFLIVKVVWGRMVCWV-LVVRRFVLVIVLENSLSSNQGPP SEQ ID NO: 50, which included a frameshift that caused an out-of frame stop codon usage.

Example 2

Characterization of RGP8.5, a Peptide that Confers MDR

Experimental Protocols:

Immunostaining and flow cytometry. $2.5 \times 10^5$ Hela cells were washed once with PBS and then incubated with 80 ml PBS buffer containing 0.1% BSA plus 20 ml monoclonal MDR-1 antibody (UIC2)-Phycoerythrin (PE) conjugate (Immunotech) at room temperature for 15 minutes. Subsequently, the cells were washed once with 2 ml PBS buffer, resuspended in 0.5 ml PBS buffer and analyzed on FACS.

Rhodamine123 efflux assay. $2.5 \times 10^5$ Hela cells were incubated in 1 ml color-free MEM with 1 mM Rhodamine123 for 15 minutes at 37° C. The cells were spun down and resuspended in 1 ml MEM without Rhodamine123 and incubated for an additional 15 minutes. The Rhodamine123 retention was analyzed on FACS (Lee, J. S. et al., (1994) *Mol. Pharmacol.*, 46, 627–638).

Cell Proliferation assay. Cells expressing the RGP8.5 peptide under the control of a tet activator were grown with or without 200 ng/ml Dox for 2 days. $5 \times 10^3$ cells were then seeded in single wells of a 96-well plate. The next day, the cells were treated with Taxol in the presence or absence of 2 mM CsA for 48 hr. The viability of Taxol-treated cells was analyzed by the Cell Proliferation Kit II (XTT, Boehringer Mannheim).

Flow cytometric analysis of cellular DNA content. The RG8.5 expressing cells were grown in the logarithmic phase. The cells were harvested, washed once with PBS and fixed in 2% paraformaldehyde pH7.4 at 4° C. for 30 minutes. After washing with 1 %BSA-PBS, the cells were resuspended in PI staining buffer containing 250 mg/ml RNase, 50 ug/ml PI, 0.1% Triton X100 in 0.1% Na Citrate pH7.4 buffer, RT for 30 min, and analyzed on FACS.

Yeast two-hybrid screening. The bait used for two-hybrid screening was RGP8.5 fused to the Gal4 DNA binding domain containing a three glycine linker/spacer. A cDNA library made from a combination of multiple human tissues (brain, lymphocyte, stomach, pancreas, liver, intestine) was used for the screening. 20 million transformants were screened. 27 His$^+$/LacZ$^+$ colonies were retrieved for further analysis.

Transfection, immunoprecipitation and western blot. A calcium phosphate transfection method was used for all transfections of test constructs into 293T cells. Cells were lysed in 200 ml of TNT buffer (20 mM Tris-HCl pH7.5, 200 mM NaCl and 1% Triton-X100), supplemented with 1 mM DTT and protease cocktail (Boehringer Mannheim). The cell extracts were incubated with 30 ml anti-flag antibody conjugated beads (Babco) at 4° C. The beads were spun down and washed with 800 ml TNT buffer for four times. For immunoprecipitation with biotinylated RG8.5 peptide, $3 \cdot 10^6$ Hela cells were lysed in a buffer containing 20 mM HEPES pH7.4, 150 mM NaCl and 1% NP40 and precleaned with a Streptavidin column (Pierce, Rockford, Ill.) to reduce non-specific binding. 3 ml of biotinylated RG8.5 peptide (1 mg/ml) in DMSO was added to the cell lysate and allowed to mix overnight at 4 ° C. Then 3 ml of Streptavidin agarose beads were added to the mixture and allowed to mix for 3 hours at 4° C. The beads were washed five times with the lysis buffer. The precipitated proteins were released from beads by boiling in 2× protein sample buffer for 5 minutes at 95° C. and resolved in 10% SDS-PAGE. For westerns, 15 ul cell extract were incubated with 5 ml of 4× protein sample buffer, boiled and separated on the gel to detect protein levels.

The proteins were then transferred to a PVDF membrane. The blot was blocked in PBS-Tween (Calbiochem) containing 5% non-fat milk, and then incubated with rabbit anti-GFP (Molecular Probe), monoclonal anti-flag antibody (Kodak ) or monoclonal anti-Zeta and anti-XAPC7 of the human 20S proteasome subunits (Affiniti, United Kingdom) at 4° C. overnight. After washing, the blots were incubated with a protein A conjugated HRP (Bio-Rad) for the rabbit primary antibody or a goat anti-mouse conjugate HRP (Santa Cruz) for the mouse primary antibody for 1 hour at room temperature. The proteins were visualized by enhanced chemiluminescent substrate (Pierce).

Results:

RGP8.5 peptide up-regulates mdr-1 gene expression in HeLa cells.

The expressed peptide might promote survival of Hela cells in a variety of manners, including action upon known regulators of apoptosis. We therefore examined the levels of endogenous anti-apoptotic proteins Bcl-2 and Bcl-xL in the presence or absence of Dox in cells expressing the RGP8.5 peptide. Both Bcl-2 and Bcl-xL remain at the same expression level in either case (data not shown), suggesting that RGP8.5 peptide-mediated Taxol resistance is not involved at this level of anti-apoptotic pathway. Thus, the peptide acts at a different level than through direct action on Bcl family protein expression levels.

One manner in which cells become resistant to Taxol is by upregulation of the P-glycoprotein MDR-1. We therefore examined whether the mdr-1 gene was up-regulated after delivery of the peptide expression construct. We transferred the RGP8.5 peptide retroviral expression vector into a naive HeLa cell population. After Taxol selection the resistant clones were pooled. We measured by FACS the expression of MDR-1 as a function of the peptide expression (using GFP as the surrogate peptide expression indicator). As shown in FIG. 2A, MDR-1 expression is apparently regulated by the expression of RGP8.5 peptide. The control peptide RGP8.2 and GFP had no effect on MDR-1 expression. A taxol resistant clone expressing the RGP8.5 peptide, designated RGP8.5.1 was examined in the presence and absence of Dox to demonstrate the efficacy of the inducible system. As can be seen expression of the MDR-1 protein is highly correlated with induction of the peptide expression construct. In an examination of several other peptides that confer a taxol resistance phenotype no other peptide gave rise (by either polyclonal or clonal examination) to induction of the MDR-1 protein at the cell surface. Thus, we conclude the effects on MDR-1 induction observed are due to expression of the insert.

We tested to determine whether survival to Taxol challenge correlated with induction of the peptide expression using Dox induction. As shown in FIG. 2B, the cells displayed strong resistance to Taxol treatment in the absence of Doxycycline (peptide expression turned on) with the clone retaining normal spreading and growth after 100 nM Taxol treatment for 48 hours. In sharp contrast, when the peptide expression was turned off the cells displayed the normal hallmarks of apoptosis and died (FIG. 2B, left panel).

To show that the MDR-1 protein was involved in the resistance mechanism observed, we pharmacologically blocked MDR-1 pump function using the well-known inhibitor of MDR-1 function, Cyclosporin A (CsA) (Volm, M, (1998) *Anticancer Res.*, 18, 2905–2917). Cells expressing the retrovirally delivered peptide were grown with or without Dox for 2 days before being subcultured to 96-well plates. Cells were then treated with Taxol in combination with high levels of CsA for 48 hours. An XTT assay for cell growth revealed that CsA could strongly repress the drug resistant phenotype (FIG. 2C) and could lead to cell death upon Taxol treatment (FIG. 2B). This result indicated that a drug pump activity was present in this clone and was a major contributor to the resistance effect observed.

We confirmed this effect visually using a Rhodamine123 efflux assay. Rhodamine 123, a fluorescent indicator dye, is actively pumped from cells expressing functional MDR-1 protein and therefore reflects MDR-1 mediated drug efflux activity (Krishan, A., et al., (1997) Cytometry, 29, 279–285). Uninfected Hela cells have very little efflux pump activity as measured by Rhodamine123 staining retention (data not shown). However, the clone containing the RGP8.5 peptide clearly was able to extrude the Rhodamine 123 and this effect was significantly diminished when peptide expression was turned off by the addition of Dox (FIG. 2D). Using R6G, an analogue of Rhodamine123, to do the efflux assay, we found the GFP positive population was associated with the pump positive peak (data not shown). Dox alone did not affect the efflux activity of other Taxol-resistant clones (data not shown), suggesting the elevated drug pump effect was solely due to the expression of the peptide.

In addition to P-gp (MDR-1), other proteins such as the multidrug resistance associated protein (MRP) and the lung resistance-related protein (LRP) has also been implicated in multidrug resistance (Leith, C., (1998) Curr. Opin. Hematol., 5, 287–291). MRP protein is expressed in the Hela tTA cell line. However, in contrast to P-gp, the RGP8.5 peptide has no effect on the levels of MRP expression in these cells (data not shown). Previous studies have also suggested that MRP overexpression does not confer resistance against Taxol (Huang, Y., et al., (1997) Leukemia, 11, 253–257). The expression of LRP in this Taxol-resistant clone was undetectable (data not shown). Taken together the data shows that peptide expression, as indicated by the GFP, is correlated with the levels of MDR1 expression. This suggests the RGP8.5 peptide has a dosage effect on the mdr-1 gene regulation, resulting in Taxol resistance. We decided, therefore, to determine the mechanism by which this occurs.

RGP8.5 modulates the mdr-1 gene expression at the RNA level.

The effect of the RGP8.5 peptide was analyzed to determine whether P-gp expression was regulated at the RNA or protein level. Steady-state mdr-1 mRNA levels were examined in a time course experiment using semi-quantitative RT-PCR. Taxol-resistant cells were incubated with doxycycline for different time periods and equal amounts of their RNA were used for RT-PCR. mdr-1 mRNA in cells expressing the peptide was detected at significantly higher levels as compared with its expression level in control HeLa cells. We observed that when peptide expression was down-regulated by growing cells in medium containing doxycycline for eight hours, the levels of mdr-1 mRNA levels declined (FIG. 3, lanes 3 and 4). When cells were exposed to Dox for more than seven days, mdr-1 mRNA was completely undetectable (FIG. 3, lane 5). However, control mRNA (tubulin), which is unaffected by Dox remained at a constant level in all cases. This suggests that RGP8.5 regulates MDR-1 protein expression at the mRNA level.

RGP8.5 peptide associates with proteasome subunits in vivo.

To identify the cellular target protein of the RGP8.5 peptide, we performed yeast two-hybrid screening using as bait the gal4 DNA binding domain fused to the peptide sequence of RGP8.5. From 20 million transformants screened, we isolated 26 positive clones, 25 of which encoded proteasome alpha type subunit XAPC7 and 1 of which encoded proteasome alpha type subunit Zeta. Both subunits are required to control substrate access to the inner chambers of the proteasome and association of the proteasome with other regulatory complexes (Groettrup, M. & Schmidtke, G., (1999) Drug Research, 4, 63–71; Kania, M., et al., (1996) Eur. J. Biochem., 236, 510–516). To confirm the binding between the RGP8.5 peptide and these subunits in mammalian cells, a GFP-RGP8.5 fusion was transfected into HeLa cells along with flag tagged XAPC7 or Zeta. A G fused to another control peptide (MG EFLIVKSGHSSGIPVGVGWCWNSAGGG EFLIVKSGPRF SEQ ID NO: 51) was used as a control. Interactions between RGP8.5 and these proteasome subunits were analyzed by co-immunoprecipitation and western blot. The GFP-RGP8.5 fusion protein was expressed at the same level in each transfection (FIG. 4A). Antibody against XAPC7 and Zeta proteins pulled down the GFP-RGP8.5 fusion (FIG. 4A, lanes 2 and 3). In contrast, the control GFP-RGP56.1 fusion protein failed to co-precipitate with XAPC7 or Zeta (FIG. 4A, lanes 5 and 6). When the GFP-RG8.5 expression vector was cotransfected with the Zeta expression plasmid, we observed a modification to the GFP-RG8.5 fusion protein. However, only the unmodified form interacted with the Zeta subunit.

To further prove that the RGP8.5 peptide binds to endogenous human proteasome subunits, the RGP8.5 peptide was synthesized in vitro and linked to beads for column biochemistry. HeLa cell extracts were then passed across these beads to purify RGP8.5 peptide binding proteins. Antibodies against XAPC7 and Zeta proteins were used to detect whether the RGP8.5 peptide was able to affinity select the endogenous proteasome and these subunits. As shown in FIG. 4B, both XAPC7 and Zeta subunits were shown to bind to RGP8.5 peptides in equimolar amounts. Thus, genetically in yeast and biochemically in mammalian cells we observe association of the RGP8.5 peptide with these proteasome subunits.

Proteasome-mediated protein degradation modulates MDR-1 gene expression.

In eukaryotic cells many biologically important pathways such as NF-kB activation and cell cycle progression are regulated by proteasome degradation via the regulation of specific factors with which they interact, as well as through action of ubiquitin (Chen, Z. et al., (1995) Genes Dev., 9, 1586–1597; Tsurumi, C., et al.,(1996) Nippon Rinsho, 54, 861–869). Given that RGP8.5 was able to regulate the MDR-1 expression and bind to proteasome subunits in mammalian cells, we examined the possibility that the peptide might function by inhibiting proteasome-mediated degradation of specific factors required for the regulation of MDR-1 expression.

To confirm that proteasome inhibitor activity of RGP8.5 was responsible for enhanced MDR-1 expression, we examined MDR-1 mRNA levels by RT-PCR in the presence of the known proteasome inhibitor MG132 (Lee, D. H. & Goldberg, A. L., (1998) Trends Cell. Biol., 8, 397403). MDR-1 mRNA levels were reduced after turning off the RGP8.5 peptide expression by the addition of Dox (FIG. 5A, lane 3). However, the level of MDR-1 mRNA was significantly enhanced under the same conditions when MG132 was added to the media (FIG. 5A, lane 4). mRNA levels for the tubulin control were unaffected by Dox or MG132. A similar result was obtained using MDR-1 antibody to detect the P-gp protein expression on the cell surface in the presence of MG132 (FIG. 5B). These results support the hypothesis that RGP8.5 modulates MDR-1 expression by binding to the proteasome and then inhibiting proteasome-mediated protein degradation. Interestingly the peptide is more effective at specifically regulating the MDR expression levels as compared to MG132. This is perhaps due to the fact that MG132 is a broad inhibitor of proteasome function and the peptide might be more specific to blocking certain target proteins from being degraded.

RGP8.5 peptide exhibits proteasome inhibitor activity.

The growth of the RGP8.5 clone was slow in our hands, suggesting there is a broader impact of the peptide on the physiology of the cell. We observed during these experiments that the GFP negative population that lost expression of the integrated virus had a faster growth rate than the GFP positive population. This suggested that the peptide had a negative impact on cell growth (data not shown). This effect is not due to the expression of GFP since other clones also expressing GFP under IRES did not show this phenotype. Although we have observed that delivery of most other peptides from the library to cells does not negatively influence observable cell physiology per se (data not shown), it was conceivable that a peptide that acts upon proteasome function might have a detrimental effect on cell growth.

Drugs that inhibit proteasome activity have been shown to affect cell cycle progression (Machiels, B. M. et al., (1997) *Cytometry*, 28, 243–252; Wojcik, C., et al., (1996) *Eur. J. Cell Biol.*, 70, 172–178). Many cell cycle regulatory factors such as p21 and cyclin B are extremely unstable, with rapidly varying intracellular levels that are controlled by proteasome-mediated proteolytic degradation during the cell cycle (Blagosklonny, M. V.,et al., (1996) *Biochem. Biophys. Re.s. Commun.*, 227, 564–569; Shirane, M. et al., (1999) *J. Biol. Chem.*, 274, 3886–3893). The degradation of cyclin B by the 26S proteasome is required for the cell cycle transition from metaphase to anaphase (Parekh, H., et al., (1997) *Biochem. Pharmacol.*, 53, 461470). To further demonstrate RGP8.5 peptide effect on inhibition of proteasome-mediated protein degradation, we compared the endogenous cyclin B protein levels in RGP8.5 expressing and non-expressing cells. Cyclin B is known to peak at G2/M. As seen in FIG. 6A, the cells expressing the RGP8.5 peptide had slightly elevated levels of cyclin B protein compared with the GFP negative cells that lacked the RGP8.5 peptide. As a control, we see that endogenous hsp70 protein in is expressed at the same level irrespective of the expression of the RGP 8.5 peptide.

A more sensitive assay of the peptide's effect could, therefore, be analysis of the cell cycle where minor fluctuations in the levels of regulatory proteins might lead to more dramatic distal cellular phenotypes. Cell cycle analysis confirmed that cells with the RGP8.5 peptide accumulate at G2/M (FIG. 6B). This strongly suggests that RGP8.5 attenuates proteasome activity, resulting in some accumulation of cyclin B protein, and, therefore, mildly blocks cell cycle progression. In order for the peptide to have been selected in our screens, this effect on the cell cycle must have been moderate. This peptide potentially, therefore, defines an interesting class of inhibitors with proteasome specificity that can be explored in later experiments.

We claim:

1. A method for screening for a resistance conferring (RC) peptide that confers multi drug resistance to a drug sensitive cell, said method comprising the steps:
   a) introducing a molecular library of retroviral vectors encoding randomized candidate peptides into a plurality of drug sensitive cells to express said randomized candidate peptides;
   b) contacting said plurality of cells with at least one chemotherapeutic drug; and
   c) screening said plurality of cells for a cell exhibiting multi drug resistance.

2. The method of claim 1 further comprising the step:
   d) isolating a cell exhibiting multi drug resistance.

3. The method of claim 2 further comprising the step:
   e) isolating a randomized candidate peptide from said cell.

4. The method of claim 2 further comprising the step:
   f) isolating a nucleic acid encoding an randomized candidate peptide from said cell.

5. A method according to claim 2 or 3 further comprising the step:
   g) identifying a target molecule using said randomized candidate peptide.

6. The method of claim 1 wherein said cells are mammalian cells.

7. The method of claim 6 wherein said mammalian cells are cancer cells.

8. The method of claim 7 wherein said cancer cells are HeLa cells.

9. The method of claim 1 wherein said chemotherapeutic drug is Taxol.

* * * * *